United States Patent
Wallach et al.

(10) Patent No.: US 8,304,384 B2
(45) Date of Patent: Nov. 6, 2012

(54) CASPASE-8 AND INFLAMMATION, INFECTION AND WOUND HEALING

(75) Inventors: David Wallach, Rehovot (IL); Rinat Abramovitch, Modiin (IL); Eitan Galun, Har-Adar (IL); Tehila Ben Moshe, Rishon Le Zion (IL); Hila Barash, Magshimim (IL)

(73) Assignees: Yeda Research and Development Co., Ltd, Rehovot (IL); Hadasit Medical Research Services and Development Ltd., Jerusalem (IL)

( * ) Notice: Subject to any disclaimer, the term of this patent is extended or adjusted under 35 U.S.C. 154(b) by 303 days.

(21) Appl. No.: 12/306,929

(22) PCT Filed: Jun. 27, 2007

(86) PCT No.: PCT/IL2007/000786
§ 371 (c)(1),
(2), (4) Date: Dec. 29, 2008

(87) PCT Pub. No.: WO2008/001370
PCT Pub. Date: Jan. 3, 2008

(65) Prior Publication Data
US 2009/0269331 A1    Oct. 29, 2009

(30) Foreign Application Priority Data

Jun. 28, 2006 (IL) .......................................... 176605
Jan. 31, 2007 (IL) .......................................... 181094

(51) Int. Cl.
*A61K 38/16* (2006.01)
*A61P 31/04* (2006.01)
*C07K 14/435* (2006.01)
(52) U.S. Cl. ........................................ 514/2.4; 530/350
(58) Field of Classification Search ................ None
See application file for complete search history.

(56) References Cited

FOREIGN PATENT DOCUMENTS

| EP | 1283052 A1 * | 12/2003 |
|---|---|---|
| WO | 03020759 A2 | 3/2003 |
| WO | WO 2007/046087 A2 * | 4/2007 |
| WO | 2007105199 A1 | 9/2007 |

OTHER PUBLICATIONS

Soung et al. Caspase-8 gene is inactivated by somatic mutations in gastric carcinomas. Cancer Res 65: 815-821, 2005.*
Oliver et al. The role of caspases in cell death and differentiation. Drug Resistance Updates 8: 163-170, 2005.*
Wallach et al. Anti-inflammatory functions of the "apoptotic" caspases. Ann Ny Acad Sci 1209: 17-22, 2010.*
XTakahashi et al. Cutting edge: Roles of caspase-8 and caspase-10 in innate immune responses to double-stranded RNA. J. immunol 176: 4520-4524, 2006.*
Soung et al. Caspase-8 gene is frequently inactivated by the frameshift somatic mutation 1225_1226delTG in hepatocellular carcinomas. Oncogene 24: 141-147, 2005.*
Lee et al. Inactivating mutations of caspase-8 gene in colorectal carcinomas. Gastroenterol 125: 708-715, 2003.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Martinon et al. Inflammatory Caspases: Linking an intracellular innate immune system to autoinflammatory diseases. Cell 117: 561-574, 2004.*
Medzhitov et al. Origin and physiological roles of inflammation. Nature 454: 428-435, 2008.*
Types of inflammation downloaded from www.glutathionediseasecure.com/type-of-inflammation.html on Dec. 17, 2011; website last updated Apr. 2011; 3 total pages.*
Ulett et al. Regulation of apoptosis by gram-positive bacteria: mechanistic diversity and consequences for immunity. Curr Immunol Rev 2(2): 119-141, 2006; 42 total pages.*
Ohya et al. Killing mechanism of Listeria monocytogenes in activated macrophages as determined by an improved assay system. J Med Microbiol 47: 211-215, 1998.*
MacFarlene et al. Nitric oxide mediates immunosuppression induced by Listeria monocytogenes infection: quantitative studies. Microbiol Pathogenesis 25: 267-277, 1998.*
Fansto et al.,"Liver Regeneration" Hepatology, 43(2) Suppl. 1, S43-S53 (2006).
McDonald et al.,"Suppression of caspase-8- and -10-associated RING proteins results in sensitization to death ligands and inhibition of tumor cell growth" PNAS, 101(16): 6170-6175 (2004).
Prosser et al.,"Molecular therapy for hepatic injury and fibrosis: Where are we?" World J Gastroenterol, 28; 12 (4):509-515.
Hainsworth et al., "Up-Regulation of Cellular Flice-Like Inhibitory Protein (CFLIP) in Brain After Traumatic Brain Injury (TBI) in Mice and Humans", Washington, DC: Society for Neuroscience, Program No. 743.3. (2003) (abstract).

(Continued)

Primary Examiner — Bridget E Bunner
(74) Attorney, Agent, or Firm — Browdy and Neimark, PLLC

(57) ABSTRACT

The present invention relates to the regulatory role of caspase-8 in infection by intracellular pathogen, inflammation and wound healing.

5 Claims, 13 Drawing Sheets

OTHER PUBLICATIONS

Guicciardi et al., "Apoptosis: a mechanism of acute and chronic liver injury" GUT, 54:1024-1033 (2005).

Selzner et al., "Mechanisms of Ischemic Injury Are Different in the Steatotic and Normal Rat Liver" Hepatology, 32(6): 1280-1288 (2000).

Oh et al., "Dexamethasone protects primary cultured hepatocytes from death receptor-mediated apoptosis by upregulation of cFLIP" Cell Death and Differentiation, 13:512-523 (2006).

Kang et al.,"Caspase-8 Serves Both Apoptotic and Nonapoptotic Roles" The Journal of Immunology, 173: 2976-2984 (2004).

Moshe et al.,"Role of Caspase-8 in Hepatocyte Response to Infection and Injury in Mice" Hepatology, 45(4): 1014-1024 (2007).

Zender, et al., "Caspase 8 small interfering RNA prevents acute liver failure in mice", *PNAS*, vol. 100, No. 13, pp. 7797-7802, Jun. 24, 2003.

Prosser et al., "Molecular therapy for hepatic injury and fibrosis: Where are we?" World J Gastroenterol, 28; 12(4):509-515, 2006.

\* cited by examiner

CASPASE-8 AND INFLAMMATION, INFECTION AND WOUND HEALING

FIELD OF THE INVENTION

The present invention relates to the regulatory role of caspase-8 in infection by intracellular pathogen, inflammation and wound healing

BACKGROUND OF THE INVENTION

The caspase family of cysteine proteases is mainly known for its pivotal role in the induction of apoptosis in animal cells (Shi et al., 2002). Some of the caspases, characterized by a 'prodomain' region located upstream of the proteolytic moiety, serve an initiating role in apoptosis. They become activated upon binding of their prodomains to death-inducing receptors or to adapter proteins associated with such receptors, and once activated they cleave other members of the caspase family, thereby activating them. Caspase-8 (previously known as MACH/FLICE/Mch4) is an initiator caspase activated within signaling complexes of receptors of the TNF/NGF family, to which it is recruited by the binding of its prodomain to an adapter protein called Fas-associated death domain (FADD; also called MORT1) (Boldin eta al., 1996, Muzio et al., 1996, and Wallach et al., 1999). Activation of caspase-8 constitutes a crucial initiating event in the apoptotic death mechanism induced by these receptors (the extrinsic cell-death pathway)(Varfolomeev et al., 1998). Both caspase-8 and FADD also contribute, by mechanisms as yet unknown, to various non-apoptotic cellular processes (e.g., see Varfolomeev et al., 1998, Zhang et al., 1998, Walsh et al., 1998, Newton et al., 1998, Alam et al., 1999, Kennedy et al., 1999, Chun et al., 2002, Sakamaki et al., 2002, Salmena et al., 2003, Kang et al., 2004, Su et al., 2005 and Beisner et al., 2005).

Although the in-vivo functioning of caspase-8 has been explored using a number of transgenic mouse models (Varfolomeev et al., 1998, Salmena et al., 2003, Kang et al., 2004, and Beisner et al., 2005), still very little is known about the enzyme's physiological or pathophysiological significance.

SUMMARY OF THE INVENTION

In one aspect, the invention relates to the use of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity, in the manufacture of a medicament for preventing and/or treating inflammation of a tissue or organ, except skin.

In another aspect, the invention relates to a method for preventing and/or treating inflammation of a tissue or organ, except skin, comprising administering to a patient in need a therapeutically effective amount of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity.

In one embodiment the tissue or organ has cells in which caspase-8 level and/or activity is down regulated.

In a further embodiment the inflammation developed following tissue or organ injury, which may be caused by resection of said tissue or organ.

In another further embodiment, the organ is the liver and caspase-8 level and/or activity is/are down regulated in hepatocytes.

In still another further embodiment the inflammatory disease disorder or condition includes, but is not limited to, hepatitis, inflammatory bowel diseases, vasculitis, joint inflammation, sinusitis, scleritis, periodontitis, cervicitis, uveitis, vulvovaginitis, conjunctivitis, alveolitis, esophagitis, acute glomerulonephritis, nephritis, acute bronchitis, acute cholecystitis, pancreatitis, and ear infection.

The invention provides the use of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity, in the manufacture of a medicament for preventing and/or treating inflammation of a tissue or organ, except skin, wherein the inflammation is manifested in a tissue or organ comprising cells in which caspase-8 level and/or activity is down regulated, and wherein inflammation develops following injury of said tissue or organ.

In addition, the invention provides a method for preventing and/or treating inflammation of a tissue or organ, except skin, wherein the inflammation is manifested in a tissue or organ having cells in which caspase-8 level and/or activity is down regulated, and wherein inflammation develops following injury of said tissue or organ, comprising administering to a patient in need a therapeutically effective amount of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity.

In a further aspect, the invention relates to the use of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity, in the manufacture of a medicament for treating an infection caused by an intracellular pathogen.

In still a further aspect, the invention relates to a method for treating an infection caused by an intracellular pathogen comprising administering to a patient in need a therapeutically effective amount of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity.

In one embodiment of the invention the intracellular pathogen include, but is not limited to, *Mycobacteria, Listeria, Leishmania, Legionella, Salmonella* and virus.

In a further embodiment of the invention the infection develops in an organ or tissue comprising cells in which caspase-8 level and/or activity is down regulated.

In a still a further embodiment of the invention the infection develops in the liver.

In yet still a further embodiment of the invention the cells in which caspase-8 level and/or activity is/are down regulated are hepatocytes.

In yet still a further embodiment of the invention the infection is caused by *Listeria*, for example, by *Listeria monocytogenes*.

In one embodiment of the invention the intracellular pathogen is a virus and therefore, the invention relates to a disease such as viral infection.

In yet still a further aspect, the invention relates to the use of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity, in the manufacture of a medicament for treating an infection caused by an intracellular pathogen, wherein infection develops in an organ or tissue comprising cells in which caspase-8 level and/or activity is down regulated.

In yet still a further aspect, the invention relates to a method for treating an infection caused by an intracellular pathogen, wherein infection develops in an organ or tissue having cells in which caspase-8 level and/or activity is down regulated, comprising administering to a patient in need a therapeutically effective amount of at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity.

It is an object of the invention to provide the use of an inhibitor of caspase-8 level and/or activity in the manufacture of a medicament for facilitating or accelerating healing of a wounded or injured tissue or organ.

It is another object of the invention to provide a method for facilitating or accelerating healing of a wounded or injured tissue or organ comprising administering to a patient in need a therapeutically effective amount an inhibitor of caspase-8 level and/or activity.

In one embodiment of the invention the wound or injury develops following tissue or organ resection.

In a further embodiment of the invention the organ is the liver.

In still a further embodiment of the invention the wound or injury develops following a physical trauma including, but not limited to, a chirurgic operation, bite, sport accident, accident, tissue or organ resection, and amputation.

It is another object of the invention to provide the use of an inhibitor of caspase-8 level and/or activity in the manufacture of a medicament for facilitating or accelerating wound healing of injured liver.

It is another further object of the invention to provide a method for facilitating or accelerating wound healing of injured liver comprising administering to a patient in need a therapeutically effective amount of an inhibitor of caspase-8 level and/or activity.

In certain embodiments of the invention, the caspase-8 inhibitor includes, but is not limited to, an antisense mRNA, small interfering RNA, a caspase-8 specific antibody, and an inhibitory small molecule.

In a further embodiment of the invention, the inhibitory molecule is a small molecule that has a molecular weight of 100 to 5,000 daltons, such as Z-IETD-FMK (SEQ ID NO:4)

It is another further object of the invention to provide the use of an inhibitor of caspase-8 level and/or activity in combination with an inhibitor of inflammation in the manufacture of a medicament for facilitating or accelerating healing of injured liver.

In one embodiment of the invention, injury develops following liver resection.

In further embodiment of the invention, ⅓ of the liver is resected.

In another further embodiment of the invention, ⅔ of the liver is resected.

In another further embodiment of the invention, the caspase-8 inhibitor is selected from a caspase-8 specific antisense mRNA, caspase-8 specific small interfering RNA, anti-caspase-8 antibody, and a caspase-8 inhibitory small molecule.

In another further embodiment of the invention, the inhibitory small molecule has a molecular weight of 100 to 5,000 daltons.

In another further embodiment of the invention, the inhibitory small molecule is Z-IETD-FMK (SEQ ID NO:4).

In another further embodiment of the invention, the inhibitor of inflammation is an agent capable of inhibiting immune cells, such as macrophages, for example, Kupffer cells.

In another further embodiment of the invention, the inhibitor of inflammation is administered after the inhibitor of caspase-8.

In another further embodiment of the invention, the inhibitor of inflammation is administered at days 1, 2, 3, 4, 5, 6, 7, 8, 9, 10, 11, or 12 days after liver resection.

In another further embodiment of the invention, the inhibitor of inflammation comprises gadolinium chloride.

BRIEF DESCRIPTION OF THE FIGURES

In all figures, black bars represent $Casp8^{F/+}$:Alb-Cre mice (with normal hepatocytes) and empty bars represent $Casp8^{F/-}$:Alb-Cre mice (with caspase-8-deficient hepatocytes).

PHx, determined by counting the hepatocytes stained (as shown in the upper panel) with anti-cyclin D1 antibody in 15 high-power fields.

FIGS. 3A-3E shows the effect of caspase-8 deficiency in hepatocytes on recovery from PHx: differential effects on volume recovery at the site of the lesion and in the rest of the liver tissue, as assessed by sequential MRI scanning and histological analysis. (A, B) Representative axial $T_1$-weighted spin-echo images of livers, acquired on day 4 post-PHx. (A) Representative image from the liver of a $Casp8^{F/+}$:Alb-Cre mouse. The dashed line outlines the ischemic area. (B) Representative image from the liver of a $Casp8^{F/-}$:Alb-Cre mouse. Arrows in A and B point to the suturing material. (C) Volume of the ischemic area expressed as a percentage of the pre-PHx liver volume at different times after PHx, demonstrating a more rapid decrease in the size of the lesion site in the $Casp8^{F/-}$:Alb-Cre mice than in controls. At least eight mice were examined in each group at each time point. (D) Post-PHx liver volume expressed as a percentage (mean±SD) of the pre-PHx in $Casp8^{F/+-}$: Alb-Cre (■) and the $Casp8^{F/-}$:Alb-Cre (O) mice, as assessed by coronal and axial MRI scans, demonstrating a more rapid size increase and abnormally large size of the liver in the caspase-8-deficient mice. *P<0.05, **P<0.01. At least eight mice per group were examined at the earlier time points (days 1-4) and at least four mice per group at the later time points. (E) Shows histological analysis of the ischemic area of a mouse liver 2 days after PHx. Upper panel-H&E-stained section of the ischemic area of the liver of $Casp8^{F/+}$ Alb-Cre mouse 2 days after PHx. In the area of the surgery there is a large focus of ghost cells and necrosis [N] of the hepatic parenchyma. Suture material [S] is seen within the necrotic area. The necrotic parenchyma is surrounded by rim of infiltrating leukocytes [I]. Lower panel, left-TUNEL staining of the area shown in the insert from the upper panel, demonstrating the massive apoptosis found in this area (staining). Above this region are dead and ghost cells (no staining), while below there are living cells (with DAPI-stained nuclei). Lower panel, right-Anti active caspase-3 immunostaining of hepatocytes located at the rim of the wounded hepatic parenchyma. Both the cytoplasm and nuclei are stained. Magnification: upper panel ×20; lower panel, left ×100; lower panel, right ×400.

Figure 4A:
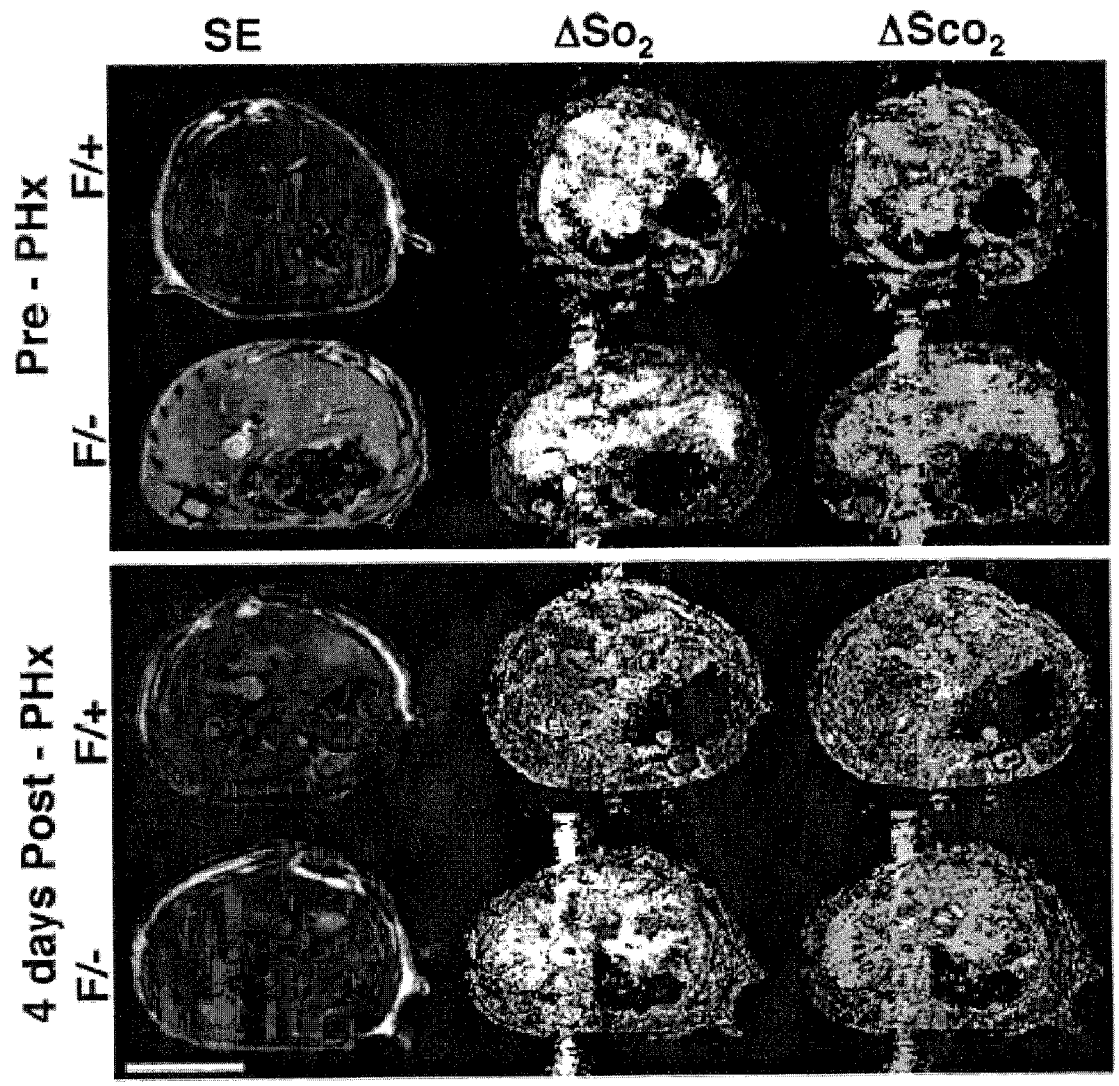
Figure 4B:
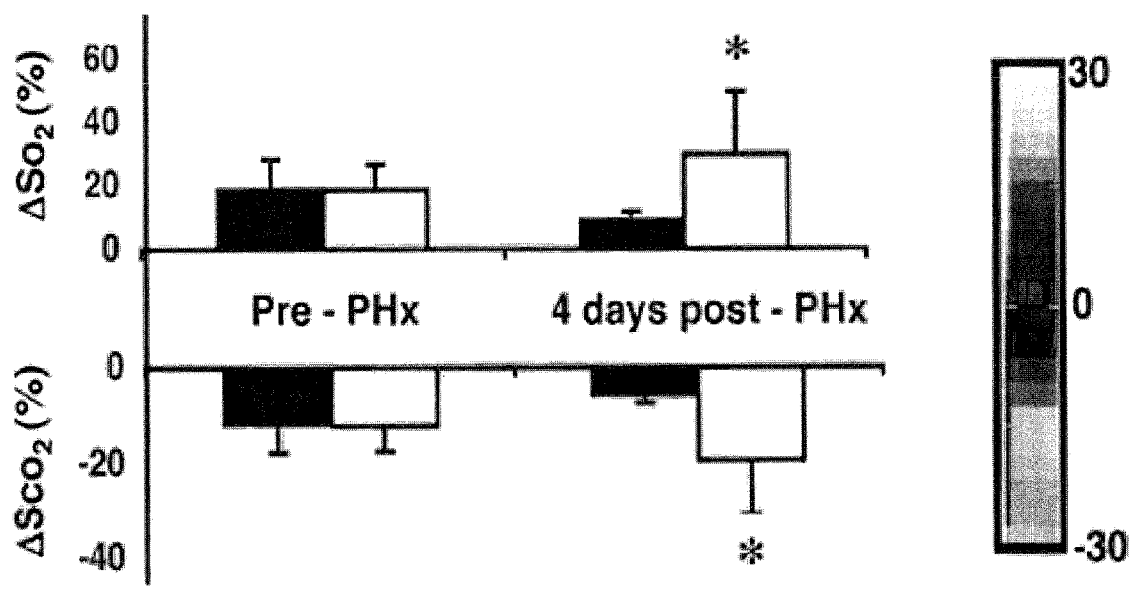

FIGS. 4A-4B show the effect of caspase-8 deficiency in hepatocytes on recovery from PHx: early perfusion and hemodynamic changes. Hemodynamic changes in the liver during regeneration were assessed by functional MRI. MRI scans were acquired before PHx and 4 days afterwards (n=4 per group at each time point). (A) Representative MRI images, $\Delta So_2$ and $\Delta Sco_2$ maps. Top rows, pre-PHx; bottom rows, 4 days post-PHx. Left column, $T_1$-weighted spin-echo images (SE); middle column, $\Delta So_2$ maps; right column, $\Delta Sco_2$ maps. Bar=1 cm. Values are as indicated in the color bar. (B) Mean $\Delta So_2$ and $\Delta Sco_2$ values±SD in $Casp8^{F/+}$:Alb-Cre (black bars) and in $Casp8^{F/-}$:Alb-Cre mice (empty bars) *P<0.02.

Figure 5A:
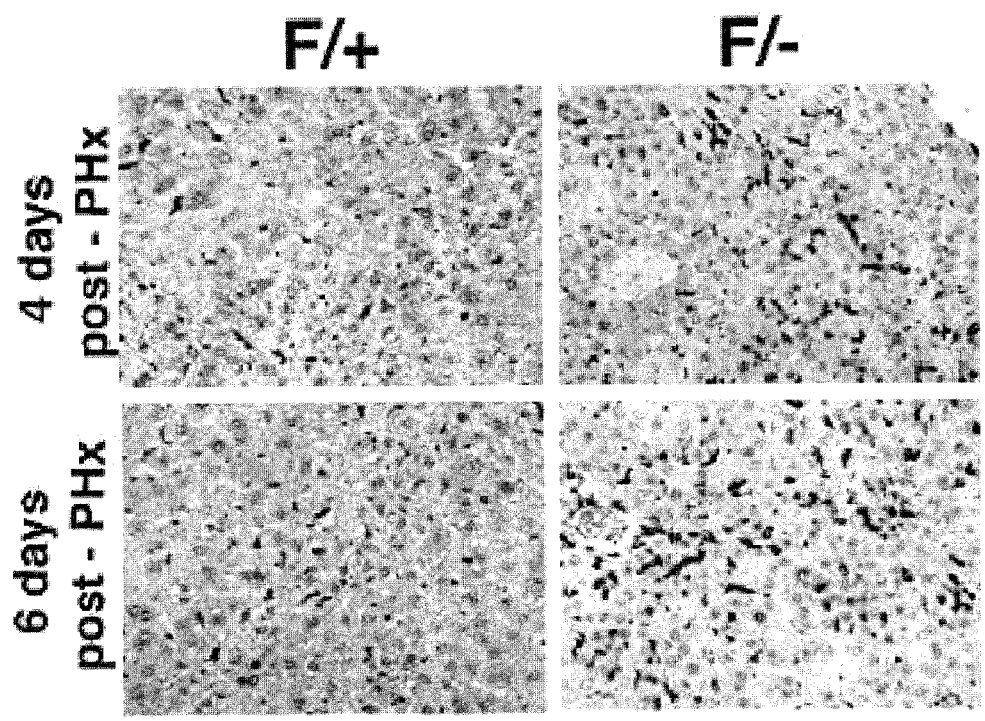
Figure 5B:
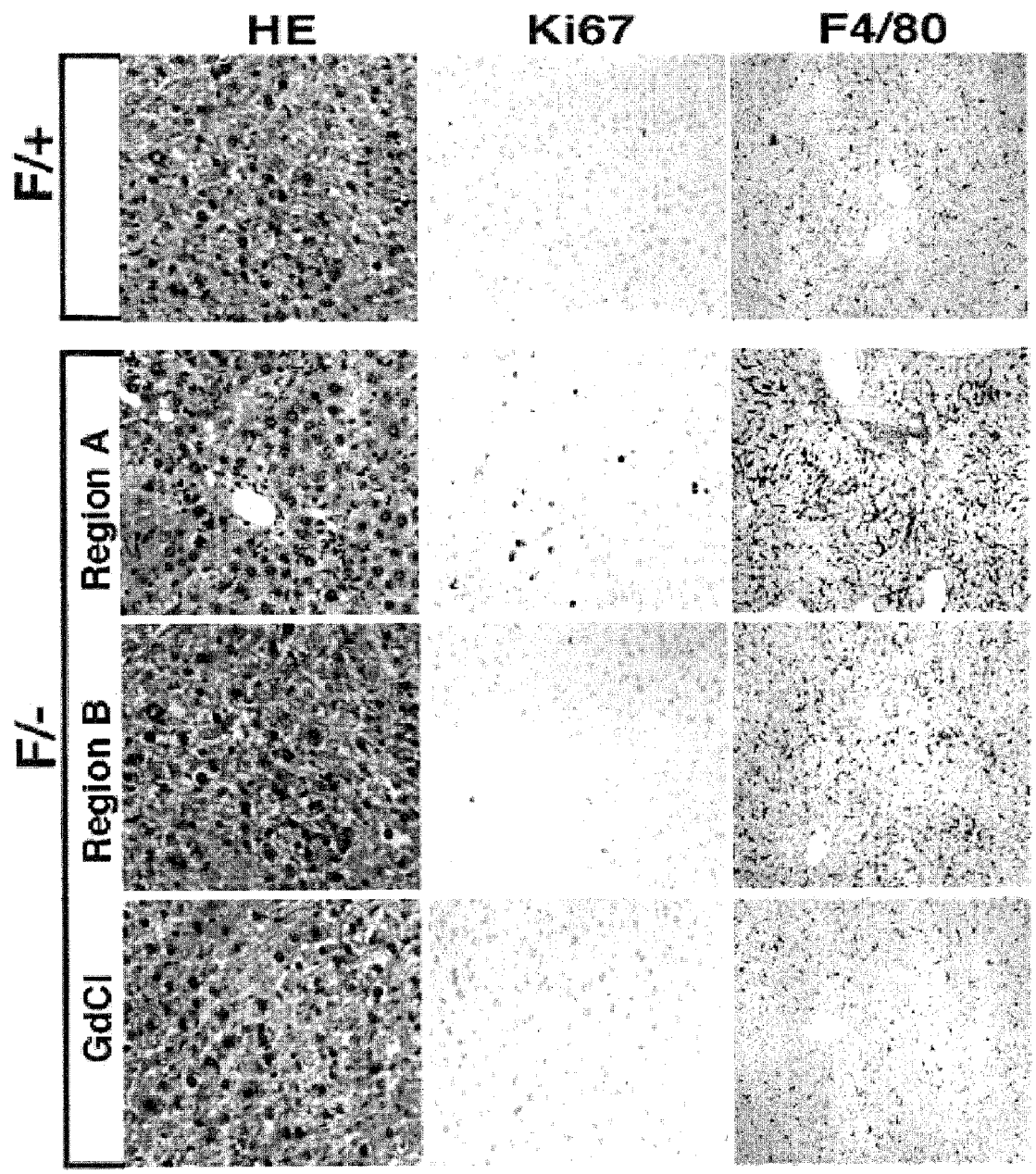
Figure 5C:
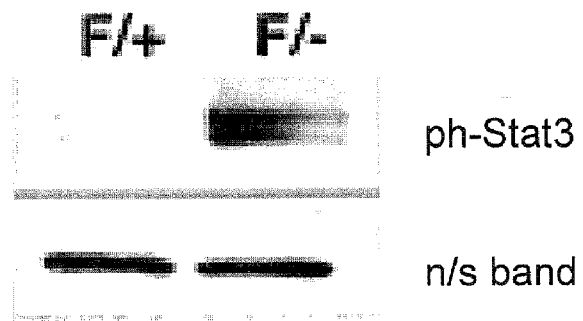
Figure 5C:
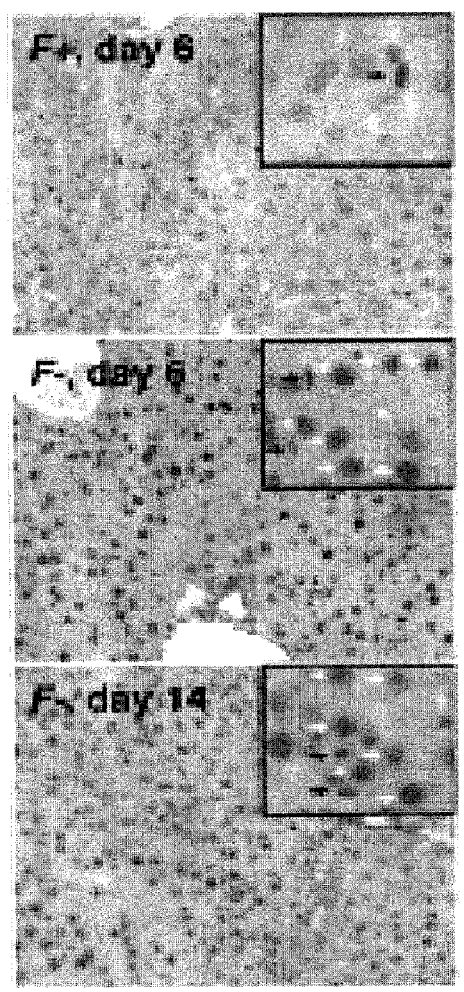

FIGS. 5A-5C show the effect of caspase-8 deficiency in hepatocytes on recovery from PHx: persistent inflammation and hepatocyte growth. (A) F4/80 immunostaining of livers 4 days and 6 days post-PHx. Magnification: ×400. (B) H&E staining and immunostaining with anti-Ki67 and anti-F4/80 antibodies 14 days after PHx of a normal liver (F/+, top), a caspase-8-deficient liver (F/−, middle, showing different regions in the same liver), and a caspase-8-deficient liver in a mouse treated with gadolinium chloride (GdCl, bottom), as described in Materials and Methods. Magnification of H&E staining, ×400; of immunostaining with anti-Ki67 antibody, ×200; and of immunostaining with anti-F4/80 antibody, ×100. (C) Upper panel, Western blotting analysis of STAT-3 phosphorylation in the liver 14 days after PHx. Lower panel, p-STAT 3 immunostaining of the liver at the indicated times post PHx. Magnification: in main panels, ×200; in insets, ×400. Black arrows, macrophages; white arrows, hepatocytes.

Figure 6A:
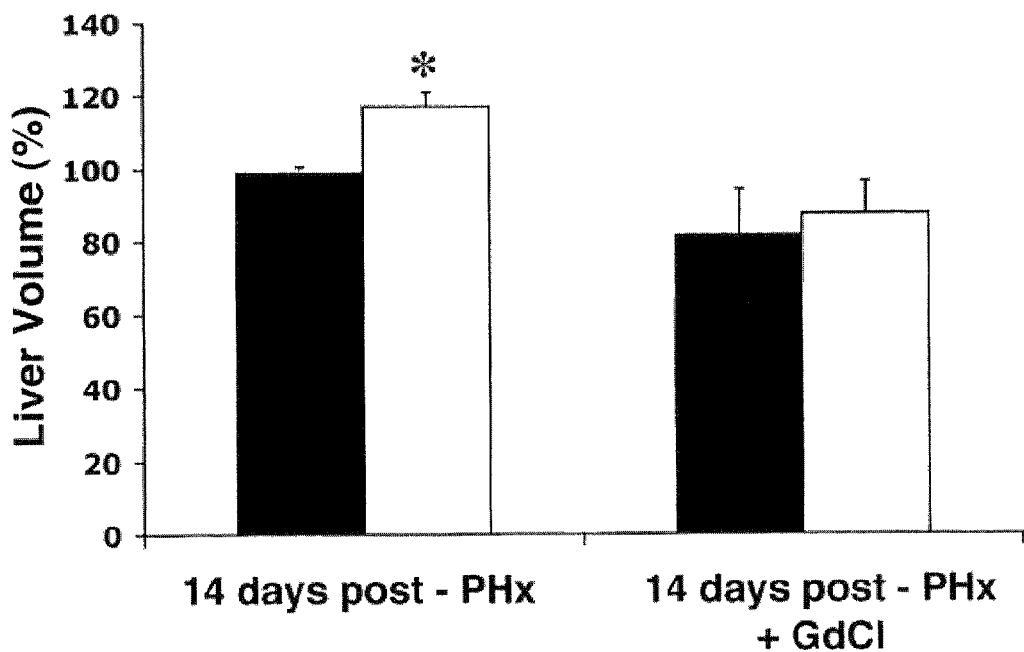
Figure 6B:
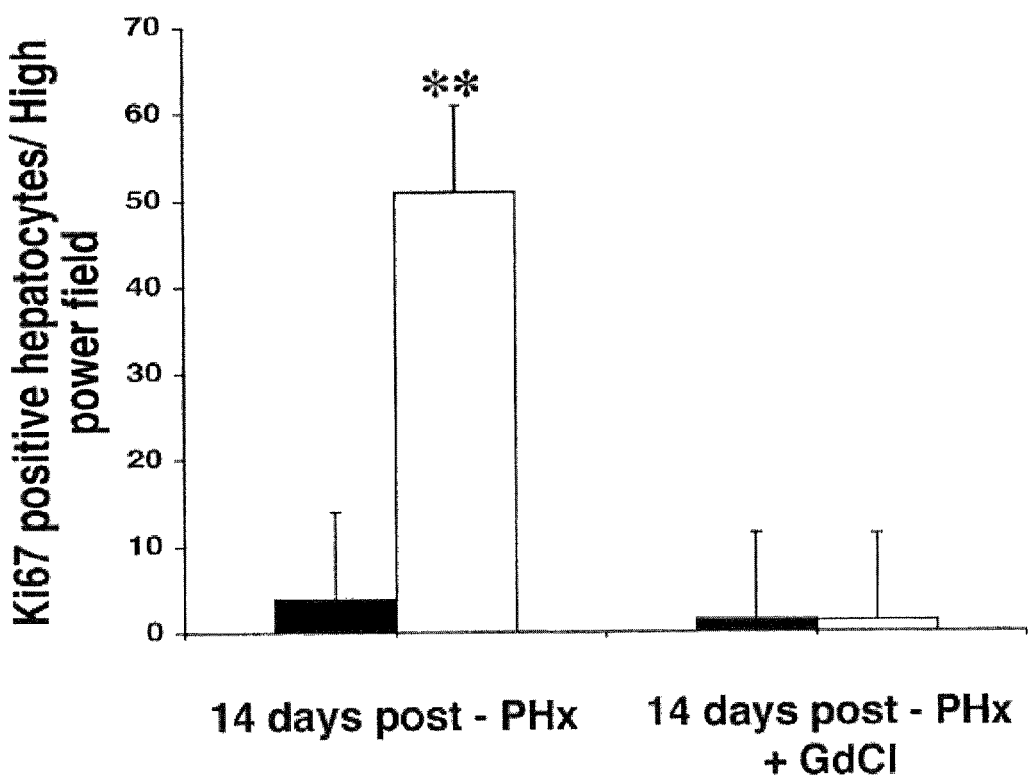

FIGS. 6A-6B show that increase in proliferation of caspase-8-deficient hepatocytes at a late stage post-PHx is secondary to inflammation. (A) Effect of gadolinum chloride treatment on the volume of livers on the $14^{th}$ day after PHx, as assessed by MRI scans, and (B) on hepatocyte proliferation at that time, as assessed by staining with anti-Ki67 antibodies and counting of the stained nuclei in 10 high-power fields. At least four mice in each group were tested. *P<0.05; **P<0.01.

DETAILED DESCRIPTION OF EMBODIMENTS

It has been found in accordance with the present invention that caspase-8 has a regulatory role in liver infection by intracellular pathogen, inflammation and healing. Therefore, the present invention relates to the regulation of the level and/or activity of caspase-8 for treating infection caused by an intracellular pathogen, treating inflammation, and facilitating healing of wounds.

The invention is based on findings obtained herein while exploring the effect of deletion of caspase-8 in hepatocytes on liver functions. It was found according to the invention that: deletion of caspase-8 in hepatocytes compromises the resistance of mice to infection by the intracellular pathogen *Listeria monocytogenes*; that partial hepatectomy (PHx) is accompanied by onset of a chronic inflammatory state in the absence of caspase-8 in hepatocytes; and that the absence of caspase-8 in hepatocytes promotes rapid healing of a lesion in the liver.

The behavior of human injured liver could be mimicked by a relevant experimental animal model, consisting of partial hepatectomy (PHx) of mice by excising the median lobe of the liver (30% PHx) or by excising the median, left, and right upper lobes (70% PHx), as described in the Examples section. It was found according to the invention, using the PHx model that absence of caspase-8 in hepatocytes affected, in several ways, regeneration of the liver after liver injury. For example, healing of the lesion in PHx occurred more rapidly in the absence of caspase-8. The improvement in healing of the lesion is observed shortly after injury induction, about two and four days after PHx. In view of these findings, one aspect of the invention relates to inhibition of caspase-8 activity and/or level to promote or facilitate healing of a lesion, injury or wound in an organ or tissue. In one embodiment, the invention relates to improving recovery of ischemic lesions by inhibiting the activity and/or level of caspase-8. In particular, the invention relates to the use of an inhibitor of caspase-8 level and/or activity for facilitating or accelerating healing of a wounded or injured tissue or organ. Wound or injury may be caused by a physical trauma including but not limited to a chirurgic operation, bite, sport accident, accident, tissue or organ resection, and amputation.

The inhibitor of caspase-8 can be used in surgical methods before during or after organ or tissue resection. Post-operative inhibition of caspase-8 treatment may have a beneficial effect on healing of post-operative lesions in the liver.

The invention contemplates the use of an inhibitor of caspase-8 before, during and/or after tissue resection for accelerating and/or facilitating healing. In one embodiment of the invention, inhibition of caspase-8 is carried out before tissue resection.

Figure 3A:
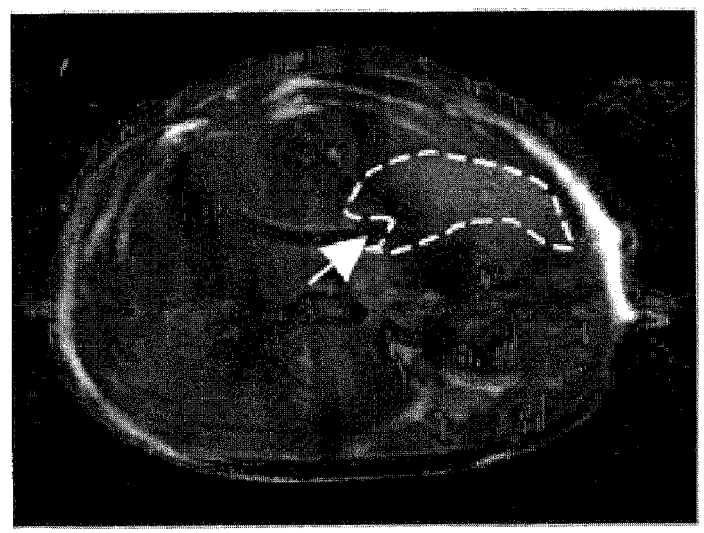
Figure 3B:
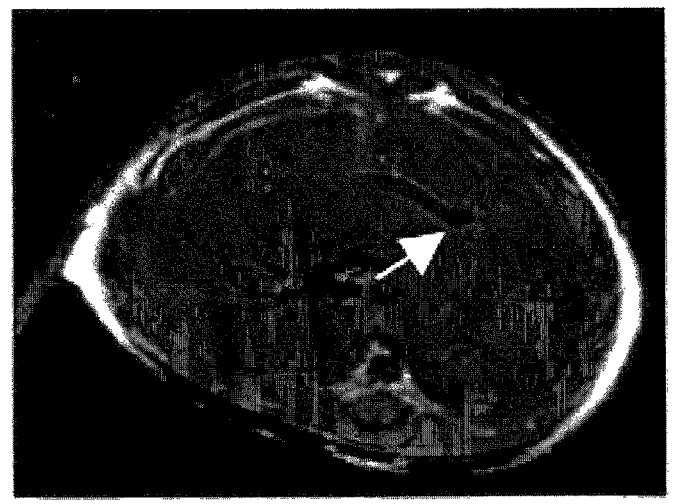
Figure 3C:
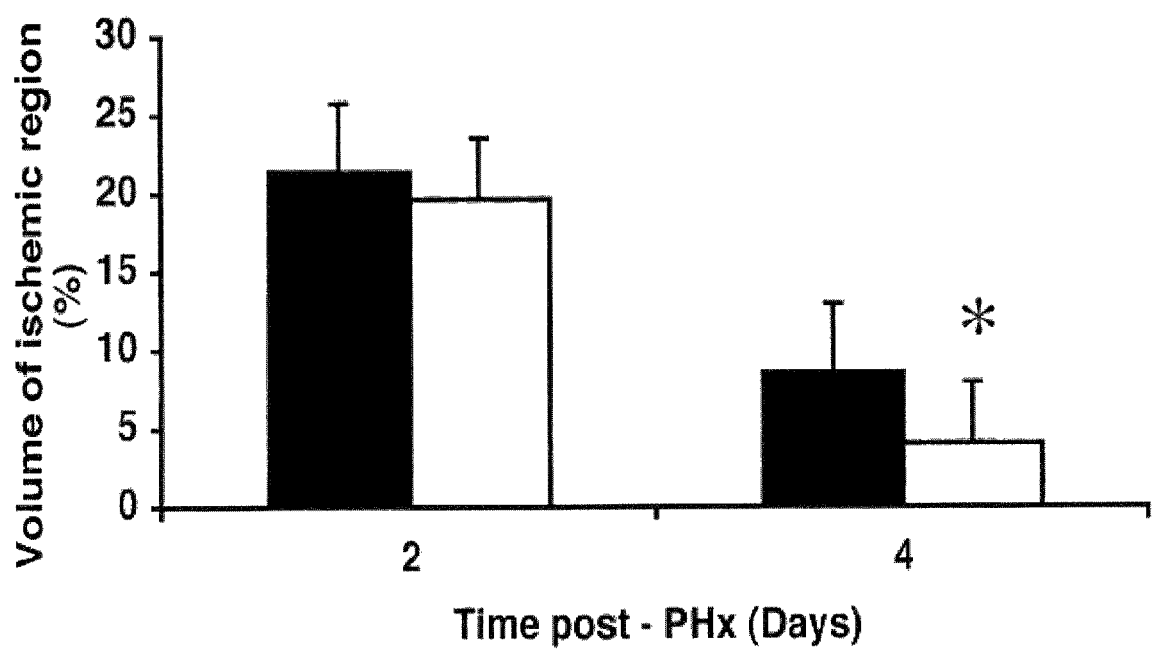
Figure 3D:
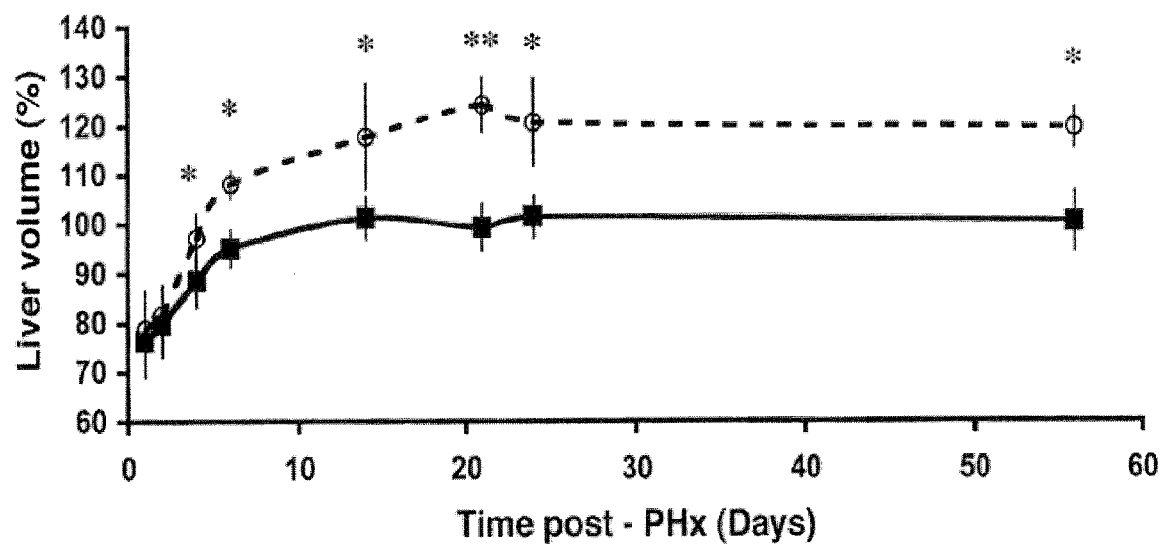
Figure 3E:

According to the present invention, a beneficial effect caspase-8 inhibition on wound healing was detected early, already a few days after injury caused by partial hepatectomy, before onset of inflammation (FIG. 3D). Therefore, an inhibitor of caspase-8 can be advantageously administered for a short period of time before, during or after injury and/or organ resection. For example, a caspase-8 inhibitor can be applied for several hours to about 1, 2, 3 days and no more than 4 days for facilitating wound healing. The inhibitor of caspase-8 can be used for 10 to 60 minutes, no less than 10, 20, 30 or 45 minutes, or for about 1, 2, 3, 4, 5, 5, 6, 7, 8, 9, 10, 11, 12, 13, 14, 15, 16, 17, 18, 19, 20, 21, 22, 23, or up to 24 hours to increase wound healing.

It was found according to the present invention that injection of gadolinium chloride (GdCl), which interferes with the function of Kupffer cells and induces their elimination, resulted in arrest of the delayed hepatocyte proliferation and prevention of hepatomegaly occurring in the prolonged absence of caspase-8 in hepatocytes. This arrest of delayed hepatocyte proliferation is particularly surprising in view of the fact that the hepatocyte proliferation facilitated early after PHx does not decrease, but rather is enhanced by GdCl treatment. Thus, for longer treatment of injured tissue with caspase-8 inhibitors, it may be of benefit using the combination of the caspase-8 inhibitor in combination with an anti inflammatory agent or an agent capable of eliminating accumulation of inflammatory cells. For example, the inhibitor of caspase-8 can be co-administered with an anti-inflammatory agent such as gadolinium chloride for up to 4 days or longer, for example, for up to 5, 6, 7, 8, 9, 10, 11, 12, 13, 14, 15, 16 days and up to 1 month for facilitating healing of wounds, tissue recovery from injury, and/or tissue regeneration.

An inhibitor of caspase-8 alone, or together with and an anti inflammatory agent or an agent capable of eliminating accumulation of inflammatory cells, can be used to facilitate healing of injured liver, liver recovery from injury, and/or liver regeneration, for example, in cases in which a malignant tumor, metastasis or cirrhotic area is removed or resected from the liver.

Liver donation between a living donor and patient presents problems because either graft or remnant liver are too small to support the life of the donor and/or recipient. Typically, a graft-to-body-weight ratio larger than 0.8 appears to be safe (Lee et al., 2004). Inhibition of caspase-8 alone, or together with and an anti inflammatory agent or an agent capable of eliminating accumulation of inflammatory cells, may allow to further extend liver resections to a liver mass below the current safety margin in the liver of a donor.

The invention contemplates the use of an inhibitor of caspase 8 administered either systemically and/or locally, at the site of the wound.

The term "inhibitor of caspase-8" within the context of this invention refers to any molecule modulating caspase-8 production and/or action in such a way that caspase-8 production and/or action is attenuated, reduced, or partially, substantially or completely prevented or blocked. The term "caspase-8 inhibitor" is meant to encompass inhibitors of caspase-8 production as well as of inhibitors of caspase-8 action. The inhibitor of caspase-8 can be targeted, for example, to hepatocytes (see below).

An inhibitor of production can be any molecule negatively affecting the synthesis, processing or maturation of caspase-8. The inhibitors considered according to the invention can be, for example, suppressors of gene expression of the caspase-8, antisense mRNAs or double stranded RNA like small interfering RNA (Hunter et al., 1975) for reducing or preventing the transcription of the caspase-8 mRNA or leading to degradation of the mRNA, proteins impairing correct folding of caspase-8, proteases degrading caspase-8, once it has been synthesized, and inhibitors of cleaving of pro-caspase-8 in order to generate active caspase-8.

An inhibitor of caspase-8 action can be an antagonist of caspase-8. Antagonists can either bind to or sequester caspase-8 molecule itself with sufficient affinity and specificity to partially or substantially neutralise the caspase-8.

Inhibitors of caspase-8 action may be caspase-8 specific antibodies, such as polyclonal or monoclonal antibodies, or any other agent or molecule preventing the binding of caspase-8 to its targets, thus diminishing or preventing triggering of the reactions mediated by caspase-8.

The term "inhibitor of a protein" within the context of this invention refers to any agent such as a protein (e.g. an antibody), polynucleotide (e.g. antisense and Small Interfering RNAs) and small inhibitory molecule capable of down-regulating the production and/or action of a protein in such a way that said protein production and/or action is attenuated, reduced, or partially, substantially or completely prevented or blocked.

A small inhibitory molecule may be an organic (carbon containing) or inorganic compound with a molecular weight of about 100 to 5,000; 200 to 5,000; 200 to 2000; or 200 to 1,000 daltons. Small molecules include, but are not limited to, metabolites, metabolic analogues, peptides, peptidomimetics, amino acids, amino acid analogs, polynucleotides, polynucleotide analogs, nucleotides, nucleotide analogs, heteroorganic and organometallic compounds. For example, caspase-8 inhibitory small molecules may be constituted of peptides that successfully compete for caspase binding. Peptides WEHD (SEQ ID NO:1), VDVAD (SEQ ID NO:2), and DEVD (SEQ ID NO:3) are examples of peptides that bind caspases. It is possible to generate reversible or irreversible inhibitors of caspase activation by coupling caspase-specific peptides to certain aldehyde, nitrite or ketone compounds. Fluoromethyl ketone (FMK) derivatized peptides, such as Z-IETD-FMK (SEQ ID NO:4), act as effective irreversible inhibitors Inhibitors synthesized with a benzyloxycarbonyl group (also known as BOC or Z) at the N-terminus and O-methyl side chains exhibit enhanced cellular permeability thus facilitating their use in vivo.

Examples of inhibitors of caspase-8 include, but are not limited to, (i) cFLIP short (CASH beta), (ii) cFLIP long (CASH alpha), (iii) the caspases-8- and -10-associated RING proteins (CARPs, McDonald ER 3rd, EI-Deiry WS, Proc Natl Acad Sci USA. 2004 Apr 20;101(16):6170-5), and (iv) a chemical inhibitor of caspase-8 such as IETD-FMK (SEQ ID NO:5) (R&D Systems Cat No. FMK007).

The term "antibody" is meant to include polyclonal antibodies, monoclonal antibodies (MAbs), chimeric antibodies, anti-idiotypic (anti-Id) antibodies to antibodies that can be labelled in soluble or bound form, and humanized antibodies as well as fragments thereof provided by any known technique, such as, but not limited to enzymatic cleavage, peptide synthesis or recombinant techniques.

A monoclonal antibody contains a substantially homogeneous population of antibodies specific to antigens, which populations contain substantially similar epitope binding sites. Mabs may be obtained by methods known to those skilled in the art. See, for example Kohler and Milstein, Nature, 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of Mabs in vivo or in situ makes this the presently preferred method of production.

Chimeric antibodies are molecules of which different portions are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al., Proc. Natl. Acad. Sci. USA 81:3273-3277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., J. Immunol. 137:1066-1074 (1986); Robinson et al., International Patent Application No. WO8702671 (published May 7, 1987); Liu et al., Proc. Natl. Acad. Sci. USA 84:3439-3443 (1987); Sun et al., Proc. Natl. Acad. Sci. USA 84:214-218 (1987); Better et al., Science 240:1041-1043 (1988); Riechmann et al., Nature 332:323-327. and Harlow and Lane, ANTIBODIES: A LABORATORY MANUAL, supra. These references are entirely incorporated herein by reference.

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully humanized antibodies and methods for their production are known in the art (Mendez et al., Nature Genetics 15:146-156 (1997); Buggemann et al., Eur. J. Immunol. 21:1323-1326 (1991); Tomizuka et al., Proc. Natl. Acad. Sci. USA 97:722-727 (2000) Patent WO 98/24893.

A monoclonal antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three-dimensional structural characteristics as well as specific charge characteristics It has been found in accordance with the present invention that hepatectomy of liver with caspase-8-deficient hepatocytes eventually triggers inflammation, and therefore, that the role of caspase-8 is associated with suppression of inflammation. This new role of caspase-8 in inflammation could not be predicted from the published literature since while caspase-12 (Saleh et al., 2006) was reported to suppress inflammatory mediators, other mammalian caspases such as caspases 1, 4, 5, 11 (Martinon et al., 2004) were reported to catalyze the generation of the inflammatory mediators IL-1 and IL-18. Although less cell proliferation was observed in caspase-8 deficient mice compared to control littermates not lacking caspase-8 few days after liver resection, later on, the effect of caspase-8 deficiency was reversed, and the caspase-8-deficient hepatocytes kept on proliferating. The excessive proliferation resulted in an abnormally enlarged liver. Our findings indicated that the sustained hepatocyte proliferation was a consequence of the inflammation. In view of these findings, the invention also relates to induction or enhancement of caspase-8 activity/level to prevent or reduce inflammation in a tissue or organ. The use of caspase-8 as an anti-inflammatory agent is advantageous, but not limited to a tissue or organ having cells in which caspase-8 level or activity is down regulated. Thus, at least one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity may be used to treat an inflammatory disease disorder or condition. Examples of inflammatory disease disorder or condition include but are not limited to, hepatitis, inflammatory bowel diseases, vasculitis, joint inflammation, sinusitis, scleritis, periodontitis, cervicitis, uveitis, vulvovaginitis, conjunctivitis, alveolitis, esophagitis, acute glomerulonephritis, nephritis, acute bronchitis, acute cholecystitis, pancreatitis, and ear infection.

The contribution of caspase-8 function to the immune response in hepatocytes, was assessed by comparing the recovery from infection at different time points after intravenous inoculation of a sublethal dose of L. monocytogenes in mice with caspase-8-deficient hepatocytes (Casp8$^{F/-}$:Alb-Cre) to that in their control littermates (Casp8$^{F/+}$:Alb-Cre). It has been found in accordance with the present invention that caspase-8 deficiency in hepatocytes attenuated the resistance of mice to the intracellular pathogen, Listeria monocytogenes.

The liver is the main site of clearance of Listeria from the circulation and is also a major site of persisting Listeria infection. Arrest of the infection is largely dependent on the ability of cells of the immune system to kill infected hepatocytes. While in the early stages after infection absence of caspase-8 in the hepatocytes seemed to have no effect on the yield of Listeria, in later stages of infection, mice with caspase-8-deficient hepatocytes show increased and persistent liver infection. Without being bound by any theory as to the operative mechanism or mode of action of caspase-8, our findings indicate that caspase-8 may help combating infection by enhancing the destruction of infected cells. However, a contribution of caspase-8 to other mechanisms of defense cannot however be excluded. The results shown herein together with a recent report showing that deletion of caspase-8 in hepatocytes endow these cells with resistance to the cytotoxic effect of the receptor Fas (Kang et al., 2004) raise the possibility that increased and persistence infection of the intracellular pathogen in the caspase-8 deficient hepatocytes is due to failure of T lymphocytes to eliminate infected hepatocytes through Fas.

Overall, using a widely employed animal model system for exploring immune defense against intracellular pathogens, it was found according to the invention that caspase-8 level and/or activity is involved in defense against intracellular pathogens in the liver and that increasing caspase-8 level and/or activity can be exploited to eradicate intracellular pathogens. In one embodiment, increasing caspase-8 level and/or activity can be used to eradicate intracellular pathogens from hepatocytes in humans.

Thus, another aspect of the invention relates to enhancing or inducing caspase-8 activity and/or level in a mammal in order to reduce infection caused by an intracellular pathogen. Examples of intracellular pathogen include, but are not limited to, *Mycobacterium, Listeria, Leishmania, Legionella, Salmonella* and virus (Steinert et al., 2002, and Gruenheid and Gros 2002). Example of mycobacterial infection includes, but is not limited to, *Mycobacterium bovis, Mycobacterium tuberculosis, Mycobacterium avium*, and *Mycobacterium lepraemurium*.

Enhancing or inducing caspase-8 activity and/or level can be affected by using one agent selected from: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity may be used to treat an inflammatory disease disorder or condition.

The caspase-8, mutein, isoform, fused protein, functional derivative, active fraction, circularly permutated derivative can be administered using an expression vector which encodes and is capable of expressing the caspase-8 or a mutein, isoform, fused protein, functional derivative, active fraction, circularly permutated derivative.

The term "agent capable of up-regulating a protein" or "activator of a protein" within the context of this invention refers to any agent or activator, such as a protein, nucleotide, polynucleotide and small molecule, capable of up-regulating said protein level and/or action.

Examples of activators of caspase-8 include, but are not limited to, FADD, caspases that can cleave caspase-8 like caspase-6 and caspase-3 and, indirectly, the various death receptors of the TNF/NGF family. Depending on the exact cellular set up, cFLIP long may also serve as caspase-8 activator.

As used herein the term "muteins" refers to analogs of a caspase-8, in which one or more of the amino acid residues of the naturally occurring components of caspase-8 are replaced by different amino acid residues, or are deleted, or one or more amino acid residues are added to the original sequence of a caspase-8, without changing considerably the activity of the resulting products as compared with the original caspase-8. These muteins are prepared by known synthesis and/or by site-directed mutagenesis techniques, or any other known technique suitable therefore.

Muteins used in accordance with the present invention include proteins encoded by a nucleic acid, such as DNA or RNA, which hybridizes to DNA or RNA, which encodes an caspase-8, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of a caspase-8, such as to have substantially similar, or even better, activity to caspase-8.

One characteristic activity of caspase-8 is its proteolytic activity at specific substrate sites. Thus, it can be determined whether any given mutein has at least substantially the same activity as caspase-8 by means of routine experimentation. As long as the mutant has proteolytic activity it can be considered to have substantially similar activity to caspase-8.

Thus it can be determined whether any given mutant has at least substantially the same activity as caspase-8 by means of routine experimentation comprising subjecting such mutant e.g. to a substrate as described in example 3 of U.S. Pat. No. 6,399,327.

In a preferred embodiment, any such mutein has at least 40% identity or homology with the sequence of caspase-8. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of caspase-8, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of caspase-8 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of caspase-8 polypeptides, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an caspase-8, or a mutein or fragment thereof, fused with another protein, which, e.g., has an extended residence time in body fluids. A caspase-8 may thus be fused to e.g., an immunoglobulin or a fragment thereof.

"Functional derivatives" as used herein cover derivatives of caspase-8, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of caspase-8, and do not confer toxic properties on compositions containing it.

These derivatives may, for example, include polyethylene glycol side-chains, which may mask antigenic sites and extend the residence of an caspase-8 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

An "active fraction" according to the present invention may e.g. be a fragment of caspase-8. The term fragment refers to any subset of the molecule, that is, a shorter peptide that retains the desired biological activity. Fragments may be readily prepared by removing amino acids from either end of the caspase-8 molecule and testing the resultant fragment for proteolytic activity. Proteases for removing one amino acid at a time from either the N-terminal or the C-terminal of a polypeptide are known, and so determining fragments, which retain the desired biological activity, involves only routine experimentation.

As active fractions of an caspase-8, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to caspase-8 e.g. proteolytic activity.

The term "salts" herein refers to both salts of carboxyl groups and to acid addition salts of amino groups of the caspase-8 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of caspase-8, e.g. proteolytic activity.

"Isoforms" of caspase-8 are proteins capable of proteolytic activity or fragment thereof, which may be produced by alternative splicing or alternative translation start-site.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

Some substances according to the invention such as peptides, proteins and oligonucleotides, necessitate their introduction into cells of a living organism. For this purpose, it is desired to improve membrane permeability of peptides, proteins and oligonucleotides. Derivatization with lipophilic structures may be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al., 1991. Further modifications of peptides and proteins comprise the oxidation of methionine residues to thereby create sulfoxide groups, as described by Zacharia et al. 1991. Zacharia and co-workers also describe peptide or derivatives wherein the relatively hydrophobic peptide bond is replaced by its ketomethylene isoester (COCH2). These and other modifications known to the person of skill in the art of protein and peptide chemistry enhance membrane permeability.

Another way of enhancing membrane permeability is the use receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al. 1998, and references therein. The CD4, GPR1, GPR15, and STRL33 molecules have been identified as receptors/co-receptors for HIV, see Edinger et al. 1998 and references therein.

Thus, conjugating peptides, proteins or oligonucleotides to molecules that are known to bind to cell surface receptors will enhance membrane permeability of said peptides, proteins or oligonucleotides. Examples for suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, proteins and oligonucleotides, and the preparation of said conjugates. Low and co-workers further show that molecules such as folate or biotin may be used to target the conjugate to a multitude of cells in an organism, because of the abundant and unspecific expression of the receptors for these molecules.

The above use of cell surface proteins for enhancing membrane permeability of a peptide, protein or oligonucleotide of the invention may also be used in targeting said peptide, protein or oligonucleotide of the invention to certain cell types or tissues. Wang et al., 1998, teaches the use of folate to target cancer cells, and Zhang et al. 1998, teaches the relative abundance of each of the other antigens noted above in various types of cancer and in normal cells.

The proteins, peptides and antisense sequences of the invention may be introduced into cells by the use of a viral vector. The use of vaccinia vector for this purpose is detailed in chapter 16 of Current Protocols in Molecular Biology. The use of adenovirus vectors has been described e.g. by Teoh et al., 1998, Narumi et al, 1998, Pederson et al, 1998, Guang-Lin et al., 1998, and references therein, Nishida et al., 1998, Schwarzenberger et al 1998, and Cao et al., 1998. Retroviral transfer of antisense sequences has been described by Daniel et al. 1998.

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., 1998 teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes, which may be used to target, said viral vector. For instance, cytokine epitopes, MHC class II-binding peptides, or epitopes derived from homing molecules may be used to target the viral vector in accordance with the teaching of the invention.

It is of advantage to target the active substances according to the invention to hepatocytes. Targeting to hepatocytes allows specific and efficient delivery of the active substances to hepatocytes. Targeting of active substances to hepatocytes can be carried out by associating the active substances to compounds or ligands that bind to and are internalized by hepatocytes, for example ligands that react with the asialoglycoprotein receptor (ASGPr) [Groman et al. 1994; Rogers & Komfeld 1971; Fiume et al. 1997], [Wu et al. 2002, Wu et al., 2004] and T7 ligand (U.S. Pat. No. 7,071,163).

The findings according to the present invention pave the way to design pharmaceutical compositions comprising an active substance capable of regulating the level and/or activity of caspase-8 in combination with at least one acceptable carrier for facilitating healing of wounds, treating inflammation, and treating infection caused by an intracellular pathogen.

The present invention provides pharmaceutical compositions including active substances according to the invention and a pharmaceutically acceptable carrier. For example, pharmaceutical compositions may comprise in case of inflammation or infection at least one of the following agents or substances of the invention: (i) caspase-8 or a mutein, isoform, fused protein, functional derivative, active fraction, circularly permutated derivative or a salt thereof; (ii) an agent capable of up-regulating caspase-8 level and/or activity; and (iii) an inhibitor of a natural inhibitor of caspase-8 level and/or activity. For example, pharmaceutical compositions may comprise in case of wound healing the following agents or substances of the invention: an inhibitor of caspase-8 level and/or activity and a pharmaceutically acceptable carrier.

The pharmaceutical compositions according to the invention are also suitable in the treatment of liver failure, consecutive to liver resection. Thus, the pharmaceutical composition according to the invention can be administrated to the donor of a liver transplantation or to patients after a liver resection, in order to prevent the establishment or progress of liver failure by facilitating and accelerating healing of the lesion. The pharmaceutical composition according to the invention, may comprise an inhibitor of caspase-8 and an anti-inflammatory agent, for example, for treating liver injury. Specific subjects to be treated by the composition of the invention include, but are not limited to, patients in which a portion of the damaged liver has been partially resected because of liver diseases such as hepatitis, hepatic cirrhosis of alcoholic, viral, drug or unknown cause, or hepatic cancer and healthy donors in which a portion of liver has been partially resected for transplantation procedures.

The pharmaceutical composition according to the present invention includes a sufficient amount of substance(s) according to the invention to achieve its intended purpose. In addition, the pharmaceutical compositions may contain suitable pharmaceutically acceptable carriers comprising excipients and auxiliaries, which facilitate processing of the active compounds into preparations which can be used pharmaceutically and which can stabilize such preparations for administration to the patient in need thereof as well known to those of skill in the art.

The substances according to the invention might be administered to a patient in need thereof in a variety of ways. The routes of administration include intraliver, intradermal, transdermal (e.g. in slow release formulations), intramuscular, intraperitoneal, intravenous, subcutaneous, oral, epidural, topical, and intranasal routes. In addition the substance can be administered together with other components of biologically active agents such as pharmaceutically acceptable surfactants, excipients, carriers, diluents and vehicles.

The dosage administered, as single or multiple doses, to an individual will vary depending upon a variety of factors, including the substance pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

The definition of "pharmaceutically acceptable" is meant to encompass any carrier, which does not interfere with effectiveness of the biological activity of the active ingredient and that is not toxic to the host to which it is administered. For example, for parenteral administration, the substance according to the invention may be formulated in a unit dosage form for injection in vehicles such as saline, dextrose solution, serum albumin and Ringer's solution.

A "therapeutically effective amount" is such that when administered, the said substances of the invention induce a beneficial effect in inflammation, infection of intracellular pathogens and wound healing. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art.

The compounds with which the invention is concerned may be prepared for administration by any route consistent with their pharmacokinetic properties.

The active substance or ingredient may also be administered parenterally in a sterile medium. Depending on the vehicle and concentration used, the drug can either be suspended or dissolved in the vehicle.

The term "dosage" relates to the determination and regulation of the frequency and number of doses.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

Having now described the invention, it will be more readily understood by reference to the following examples that are provided by way of illustration and are not intended to be limiting of the present invention.

EXAMPLES

Material and Methods (i) Mouse Strains. The strains of mice carrying a knocked out caspase-8 allele ($Casp8^{-/+}$) (Varfolomeev et al., 1998) or a conditional caspase-8 allele ($Casp8^{F/+}$) (Kang et al., 2004), as well as the mice expressing Cre under control of the liver-specific albumin promoter (Alb-Cre) (Kellendonk et al., 2000) and their use for deletion of the caspase-8 gene specifically in hepatocytes (Kang et al., 2004), have been described previously. The experiments relating to *Listeria* infection were carried out with mice of pure C57B1/6 background, obtained by 11 backcrossings with mice of that strain. The presented experiments relating to post-PHx regeneration of the liver were performed with mice of the original mixed genetic background and pure C57B1/6 background, as indicated. All mice were kept in a specific pathogen-free facility. Mice were handled according to the criteria outlined in the "Guide for the Care and Use of Laboratory Animals" prepared by the National Academy of Sciences and published by the National Institutes of Health. All experiments were approved by the institutional animal ethical care committee.

(ii) *Listeria monocytogenes* Infection and Quantification. Mice were injected intravenously with $2 \times 10^3$ plaque-forming units of *Listeria monocytogenes* (strain 10403S) and killed at different times afterwards. Their livers and spleens were removed and weighed. Portions of livers and spleens were weighed and homogenized separately in 1% Triton X-100 in phosphate buffered saline (PBS). Serial 10-fold dilutions of organ homogenates were plated on brain heart infusion agar. Numbers of colony-forming units per organ were determined after incubating the agar plates at 37° C. for 24 hours. The remaining parts of the spleens and livers were fixed in 10% neutral buffered formalin for 24 to 48 hours. The tissues were then trimmed, processed routinely in paraffin, and stained with hematoxylin and eosin (H&E) or with anti Ki67 antibody (DakoCytonation, Glostrup, Denmark).

(iii) Partial Hepatectomy and Gadolinium Chloride Administration. Age-matched $Casp8^{F/-}$: Alb-Cre mice and $Casp8^{F/+}$: Alb-Cre mice were lightly anesthetized with intraperitoneally (i.p.) administered xylazine 10 mg/g body weight (Chanelle Pharmaceuticals Manufacturing, Loughrea, Galway, Ireland) and ketamine 450 mg/g body weight (Fort Dodge Animal Health, Fort Dodge, Iowa). It was performed 'one-third' (30%) PHx by excising the median lobe of the liver, and 'two-thirds' (70%) PHx by excising the median, left, and right upper lobes as described (Higgins et al., 1931 and Greene et al., 2003). Mice were imaged before PHx and afterwards on days 0-56 (every other day during the first week and weekly from then on). On days 10 and 12 after PHx the mice were injected i.p. with gadolinium chloride (Sigma-Aldrich, St. Louis, Mo.) in saline at a dosage of 10 mg/kg.

(iv) MRI Analysis Technique. Magnetic resonance imaging (MRI) experiments were performed using a horizontal 4.7 T Biospec spectrometer (Bruker Medical, Ettlingen, Germany) with a 4.2-cm birdcage coil. Mice were anesthetized (with pentobarbital 30 mg/kg, i.p.) and placed supine with the liver located at the center of the coil. Liver volume was determined from multi-slice coronal and axial T1-weighted spin echo images (repetition time=400 ms; echo time=18 ms; slice thickness=1 mm). In brief, the liver boundary visualized in each slice was outlined using image-processing software (NIH Image). To convert the number of liver pixels to an area we multiplied by the factor $[(\text{field of view})^2/(\text{matrix})^2]$. The total liver volume was calculated as the summed area of all slices, multiplied by the slice thickness. For each mouse the liver volume was expressed as a percentage of the preoperative liver volume.

Hepatic perfusion and hemodynamics were evaluated from T2*-weighted gradient echo images (repetition time=100 ms; echo time=10 ms; field of view=3.4 cm; slice thickness=1.2 mm) acquired while the mouse was breathing air, air and $CO_2$ (95% air, 5% $CO_2$), and carbogen (95% $O_2$, 5% $CO_2$), as previously described (Abramovitch et al., 1998, and 1999). Five repeats were acquired for each gas mixture.

The MRI hemodynamics data were analyzed on a PC computer using IDL software (Research Systems, Boulder, Colo.). Maps of the mean signal intensity $$\Delta S_{CO_2} = \frac{\overline{S}_{CO_2} - \overline{S}_{air}}{\overline{S}_{air}} \times 100$$

$$\Delta S_{O_2} = \frac{\overline{S}_{O_2} - \overline{S}_{CO_2}}{\overline{S}_{CO_2}} \times 100$$

values for each pixel obtained during inhalation of the different gases ($S_{air}$, $Sco_2$ and $So_2$) were calculated from the average of four values for each gas (values obtained during gas changes were discarded). The percentage change in the intensity of the MRI signal induced by hypercapnia ($\Delta Sco_2$) and by hyperoxia ($\Delta So_2$) was calculated according to the following equations:

Results are expressed as means±SD. Mean values were calculated from regions of interest in n mice as indicated and from three slices per mouse.

(v) Calculation of the Volume of the Ischemic Area. Surrounding the dissected area, an abnormal zone manifesting a signal intensity higher than that of healthy liver tissue was detectable by MRI. This area was termed the "ischemic zone" and its borders and volume was determined. The volume in each mouse was calculated as the sum of the areas of high signal intensity in all slices multiplied by the slice thickness. The volume of the ischemic zone was calculated as a percentage of the pre-PHx liver volume on days 2 and 4 post-PHx.

(vi) Statistical Analysis. Differences between groups were identified by the unpaired Student's t-test. A value of $P<0.05$ was considered statistically significant.

(vii) Histology and Immunostaining. Livers were fixed in 10% neutral-buffered formalin, embedded in paraffin, cut into 4-µm sections, and stained with H&E. To detect cells expressing processed caspase-3 the sections were deparaffinized, rehydrated, and incubated with rabbit anti-mouse cleaved caspase-3 (Asp 175) antibody (Cell Signaling Technology, Beverly, Mass.), according to the manufacturer's instructions. Sections were then stained with biotinylated peroxidase anti-rabbit antibody (DAKO Envision+System, Glostrup, Denmark).

To detect cells expressing Ki67 the liver paraffin sections were deparaffinized, rehydrated, and denatured for 10 minutes in boiling 10 mM citric acid (pH 6.0). They were allowed to cool to room temperature for 20 minutes, and then washed three times in PBS. After treatment for 5 minutes in 3% H2O2 the slides were incubated overnight at 4° C. with rat anti-mouse Ki67 antibodies diluted 1:100 in CAS-Block (Zymed Laboratories, San Francisco, Calif.). They were then washed three times with PBS, incubated for 1 hour with immunoperoxidase polymer anti-rat (Nichirei Biosciences, Tokyo, Japan), and developed with 3,3'-diaminobenzidine (Sigma-Aldrich) for 10 minutes.

Cells expressing F4/80 were detected similarly, using rat anti-mouse F4/80 antibody (Serotec Oxford, UK), except that for antigen retrieval the paraffin sections were treated for 3 minutes at room temperature with a solution containing 20 mM Tris (pH 7.5), 0.1% trypsin, and 0.1% calcium chloride. The macrophage content of the livers was determined by quantifying the F4/80 positive areas in the slides using the ImageJ 1.37r software.

Bromodeoxyuridine (BrdU) was injected i.p. 3 hours before the mice were killed, and was detected with the aid of an Amersham cell-proliferation kit (Amersham Biosciences, Piscataway, N.J.), according to the manufacturer's instructions.

For immunohistochemical detection of the phospho signal transducer and activator of transcription 3 protein (p-STAT 3, a signaling protein activated during inflammation) the paraffin sections were deparaffinized, rehydrated, incubated for 10 min in 3% hydrogen peroxide to quench endogenous peroxidase, and then subjected to antigen retrieval by boiling for 15 min in 1 mM EDTA (pH 8.0). The slides were then washed three times with TBS+0.5% Tween 20 (TBST) and incubated overnight at 4° C. with rabbit anti mouse p-STAT 3 (Tyr705) antibody (Cell Signaling Technology, 1:500). After a series of rinses in TBST they were incubated in biotinylated goat anti-rabbit secondary antibody (Jackson ImmunoResearch Laboratories, West Grove, Pa.). Bound antibody was detected using the TSA Biotin System (Perkin Elmer, Boston, Mass.). Immunoreactivity was visualized after incubation for 5-10 minutes with 3-amino-9-ethylcarbazole high-sensitivity substrate-chromogen (Dako).

(viii) Western Analyses. At different times after PHx the liver tissue was removed, frozen immediately in liquid nitrogen, and stored at −80° C. till use. Samples of 0.3 mg of the frozen tissue were weighed and homogenized in homogenization buffer [50 mM β-glycerophosphate pH 7.3, 1.5 mM EGTA, 1 mM EDTA, and 1 mM dithiothreitol containing 1' complete protease inhibitor cocktail (Roche Diagnostics, Mannheim, Germany)], fractionated on 10% sodium dodecyl sulfate polyacrylamide gels, blotted to nitrocellulose, and incubated overnight at 4° C. with rabbit anti-mouse cyclin A antibody, rabbit anti-mouse phospho STAT-3 antibody (both from Santa Cruz Biotechnology), rabbit anti-mouse cyclin E antibody (Upstate, Chicago, Ill.), rabbit anti-mouse phospho-Rb antibody (Cell Signaling Technology), rat anti-mouse caspase-8 monoclonal antibody (1G12, kindly donated by Drs A. Strasser and L. A. O'Reilly, WEHI, Melbourne, Australia), or monoclonal anti-β-actin antibody (Sigma). This was followed by incubation with horseradish peroxidase-conjugated secondary antibody (Jackson ImmunoResearch Laboratories, West Grove, Pa.), diluted 1:5000. Specific bands were visualized by chemiluminescence.

Example 1

Caspase-8 Deletion in Hepatocytes Compromises Resistance to *Listeria* Infection The liver is a major site of replication of *L. monocytogenes*, a Gram-positive bacterium that invades the cytoplasm of eukaryotic cells and multiplies in it. Eradication of this pathogen from the liver after experimental infection of mice is therefore widely used as a model system for studying mechanisms of immune defense against intracellular pathogens (Wing et al., 2002). To examine the contribution of caspase-8 function to the immune response in hepatocytes, the recovery from infection was compared at different time points after intravenous inoculation of a sublethal dose of *L. monocytogenes* in mice with caspase-8-deficient hepatocytes ($Casp8^{F/-}$:Alb-Cre) to that in their control littermates ($Casp8^{F/+}$:Alb-Cre).

Figure 1A:
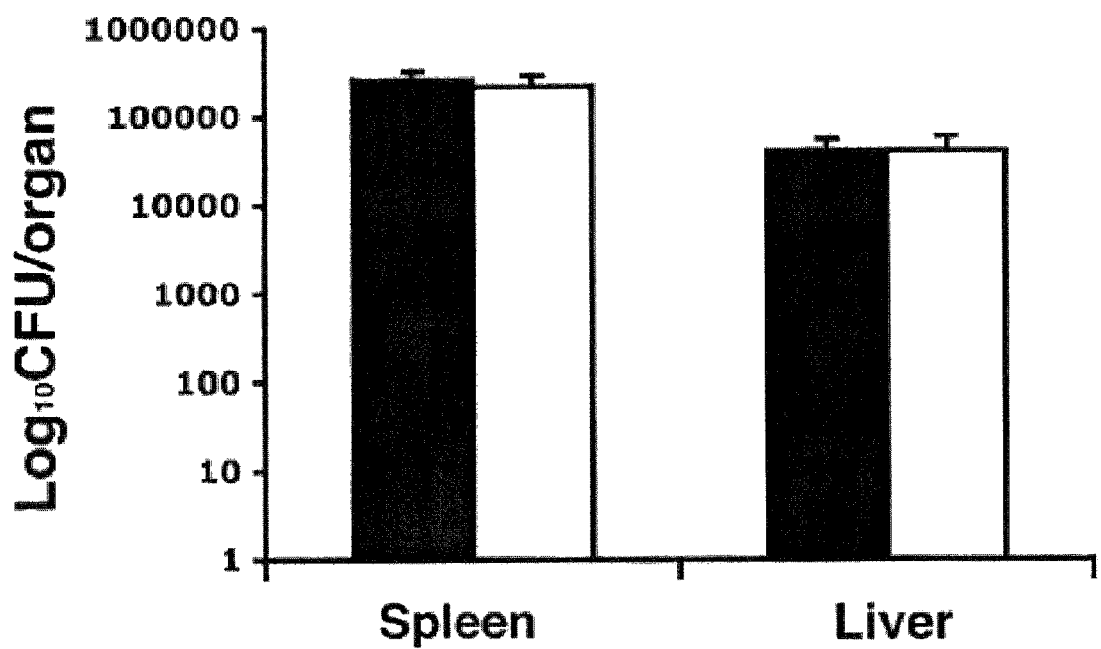
FIGS. 1A-II show the effect of caspase-8 deficiency in hepatocytes on *Listeria Monocytogenes* infection. (A C) Viable *Listeria* organisms recovered from mouse spleens and livers after sublethal infection at 24 hours (A), 6 days (B) and 14 days (C) after infection. Each group of F/+or F/−mice at each time point comprised at least five mice. (D-I) Histological analysis of liver sections from $Casp8^{F/-}$:Alb-Cre and $Casp8^{F/+}$:Alb-Cre mice 6 and 14 days after *Listeria* infection. (D, E) H&E staining of livers 6 days post-infection, demonstrating accumulation of leukocytes in the livers of $Casp8^{F/-}$:Alb-Cre mice (arrows). (F, G) At 14 days post-infection the livers of $Casp8^{F/-}$:Alb-Cre mice (G) exhibit large necrotic lesions, whereas control livers appear normal. (F) Magnification (×200) of D through G. (H, I) Anti-Ki67 immunostaining of livers 14 days post-infection, demonstrating large numbers of proliferating hepatocytes in $Casp8^{-}$:Alb-Cre, but not in $Casp8^{F/+}$:Alb-Cre livers (I; brown-stained nuclei). Magnification: ×100.
Figure 1B:
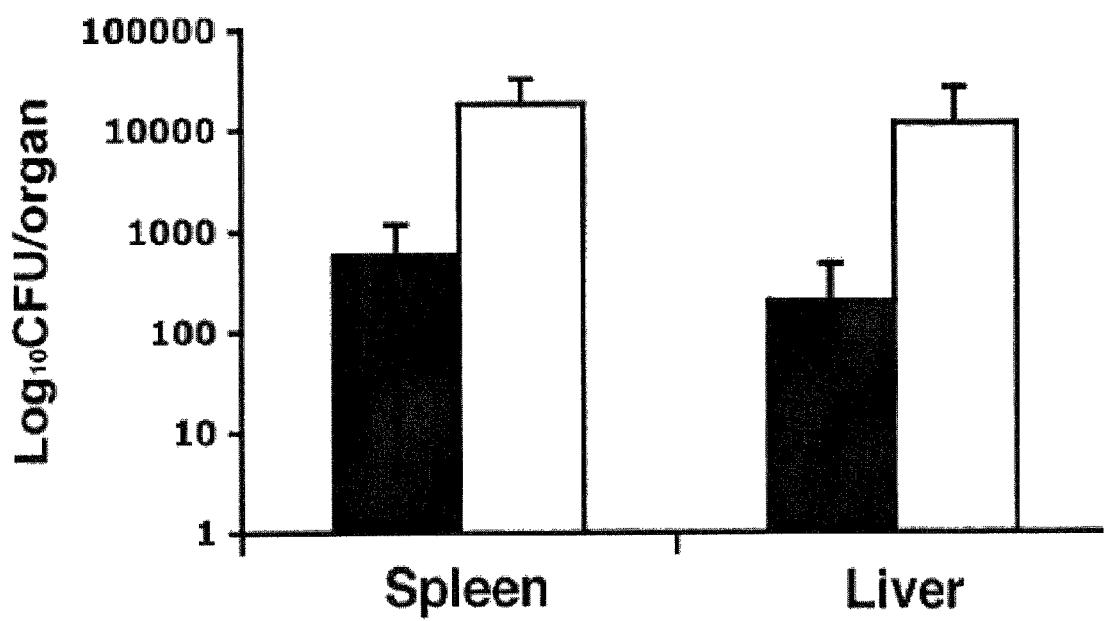
Figure 1C:
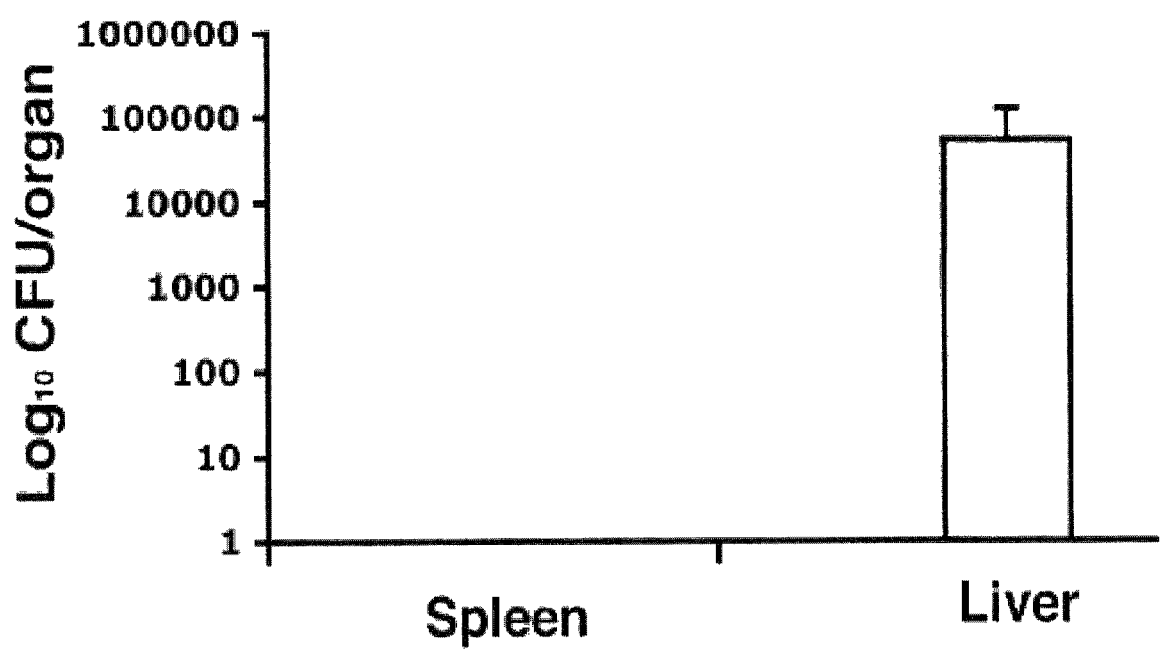
Figures 1D, 1E, 1F, 1G, 1H, 1I:
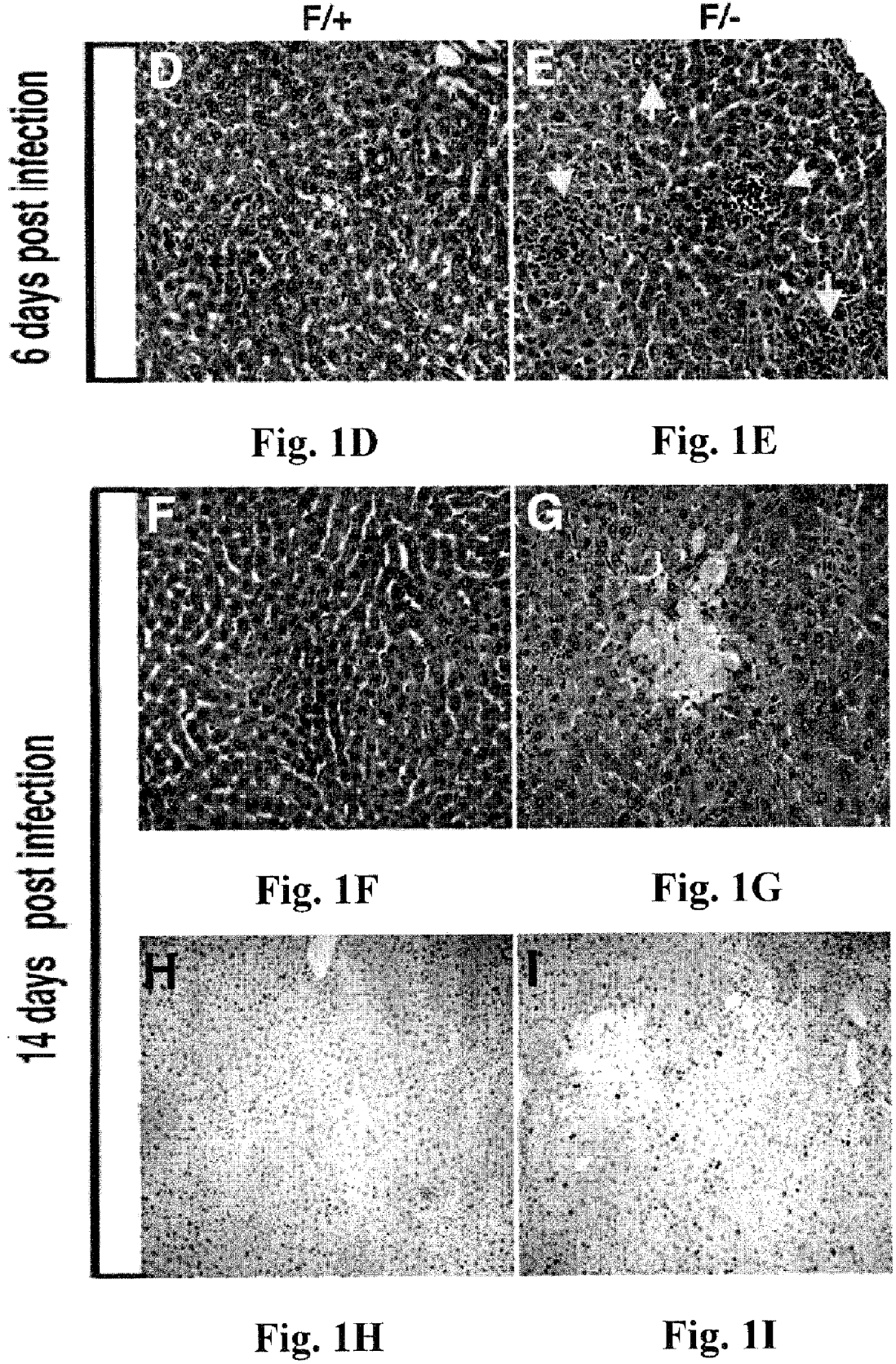

One day after infection, bacterial loads in the organs of the $Casp8^{F/-}$:Alb-Cre mice were similar to those in their control littermates. On the $6^{th}$ day, however, bacterial titers in both the livers and spleens of the $Casp8^{F/-}$:Alb-Cre mice were 10- to 100-fold higher than in the controls (FIG. 1A, B). By the $14^{th}$ day the pathogen had been totally cleared from both livers and spleens of the control mice, whereas titers in the livers of the $Casp8^{F/-}$:Alb-Cre mice remained high (FIG. 1C). The prolonged infection resulted in inflammation (FIG. 1D, E) and development of necrotic lesions in the liver (FIG. 1F, G), as well as increased proliferation of hepatocytes (FIG. 1H, I). By the $6^{th}$ day post-infection about 15% of the $Casp8^{F/-}$:Alb-Cre mice, but none of the control mice, had died.

Example 2

Effects of Caspase-8 Deficiency in Hepatocytes on Recovery from PHx: Attenuation of the Early Growth Response To evaluate the contribution of caspase-8 to tissue recovery from injury, the effect of caspase-8 deletion from hepatocytes on liver regeneration after PHx was assessed. Consistently with prior reports, it was found that PHx prompts a burst of hepatocyte proliferation (reviewed in Fausto et al., 2006). In the livers of $Casp8^{F/-}$:Alb-Cre mice, however, proliferation, and also the induction of several molecular changes associated with G1/S transition (increased expression of cyclin A, D and E, and phosphorylation of the retinoblastoma protein) occurred to a significantly lesser extent than in their control littermates (FIG. 2). This decrease was observed after ⅓ PHx as well as after ⅔ PHx, which leads to more robust and better synchronized DNA synthesis and more effective progression through the cell cycle (Mitchell et al., 2005 19). Because mortality during the first few hours post-resection was significantly higher after ⅔ PHx, all subsequent analysis of the effect of caspase-8 deficiency were restricted to recovery of mice from ⅓ PHx.

Example 3

Effects of Caspase-8 Deficiency in Hepatocytes on Recovery from PHx: Improved Recovery of the Ischemic Lesion Site The strict control of cell growth in vivo is impressively manifested by the ability of the liver to maintain its normal size and the accurate recovery of its original size following dissection (Diehl 2000, and Michalopoulos and DeFrances, 1997). In various pathological conditions, however, this control fails, resulting in abnormal enlargement (hepatomegaly) (Adachi et al., 1995, Anders et al., 2005 and Zimmers et al., 2003). To further assess the effect of caspase-8 deficiency on recovery of the liver after PHx changes in liver volume was monitored by the use of MRI. Prior to hepatectomy, the average liver volume in the $Casp8^{F/-}$:Alb-Cre mice was identical to that in the $Casp8^{F/+}$:Alb-Cre mice (data not shown). After PHx, however, the two groups differed significantly in their kinetics of liver growth (FIG. 3C). On $T_1$-weighted spin echo MRI, two regions were distinguishable in the hepatectomized livers: the ischemic lesion site that was generated as a consequence of the dissection, and which was found on histological analysis to contain necrotic tissue as well as apoptotic cells (FIG. 3E), whose size gradually decreased during regeneration; and the rest of the liver, which increased in size to compensate for the loss of the dissected tissue. The decrease in size of the ischemic lesion site in the Casp8$^{F/-}$:Alb-Cre mice was significantly more rapid than that in the control mice (FIG. 3A-C), suggesting that absence of caspase-8 in the hepatocytes promotes rapid healing or adsorption of the tissue at that site.

Example 4

Effects of Caspase-8 Deficiency in Hepatocytes on Recovery from PHx: Persistent Late Hepatocyte Proliferation Surprisingly, although the initial proliferative response of the caspase-8-deficient hepatocytes was milder than that of the normal hepatocytes, the increase in size in the rest of the liver in the Casp8$^{F/-}$:Alb-Cre mice was not slower than that in their control littermates, but significantly faster. Moreover, whereas the liver in control mice stopped growing once it reached its original size, the eventual size of the liver in the Casp8$^{F/-}$:Alb-Cre mice was significantly larger than normal (FIG. 3D), reaching 120% of the pre-PHx size.

Figure 2A:
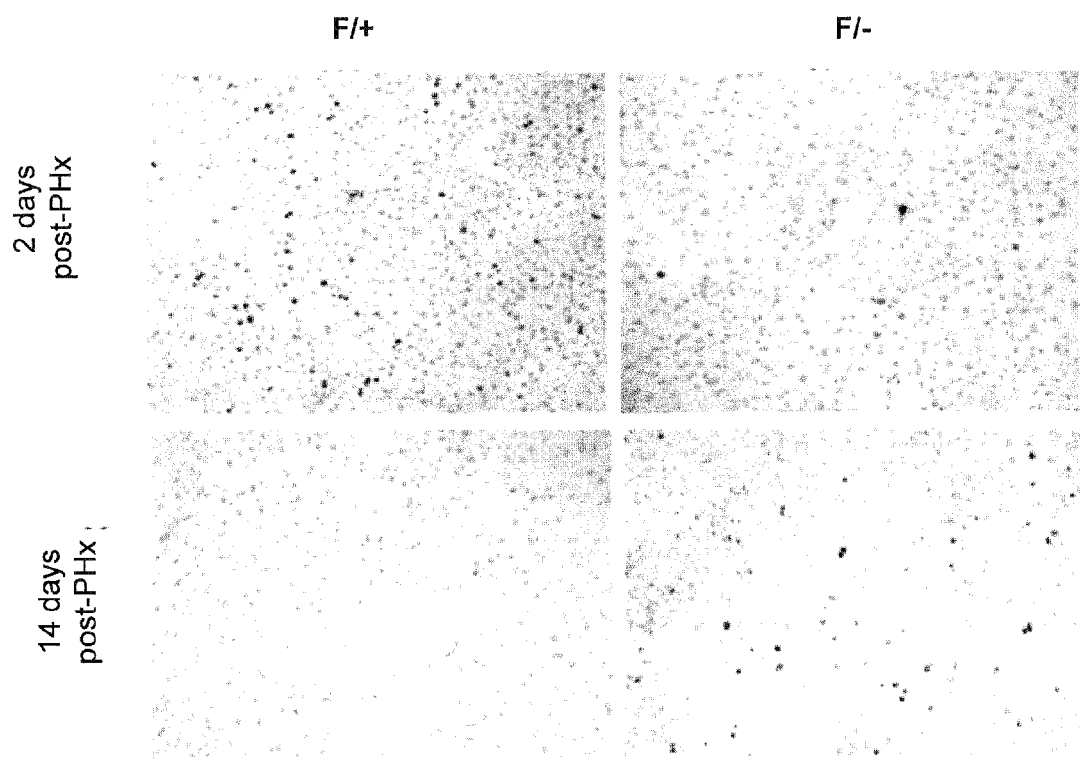
FIGS. 2A-2E show the effect of caspase-8 deficiency in hepatocytes on recovery from PHx: a decrease in early growth response. (A) Anti-Ki67 immunostaining (brown-stained nuclei) of the liver at early (day 2) and late (day 14) stages after PHx. Magnification: ×100. (B, C) Hepatocyte proliferation at various time points following ⅓ (B) and ⅔ PHx (C), quantified by determining the number of hepatocytes stained with antibodies against Ki67 (or BrdU; inset), as shown in A, counted in 10 high-power fields. *P<0.05, **P<0.01. At least eight mice were tested at each time point in four independent experiments. (D) Amounts of various G1/S-transition associated proteins (cyclin A, cyclin E, phosphorylated retinoblastoma protein) in the liver at different time points after ⅓ PHx (left panel), ⅔ PHx (right panel). Shown are representative results of tests carried out in at least four mice at each time point. (E) Upper panel, anti-cyclin D1 immunostaining 2 days after ⅓ PHx. Magnification: ×400. Lower panel, quantification of the increase in cyclin D1, 2 and 4 days after ⅓
Figure 2B:
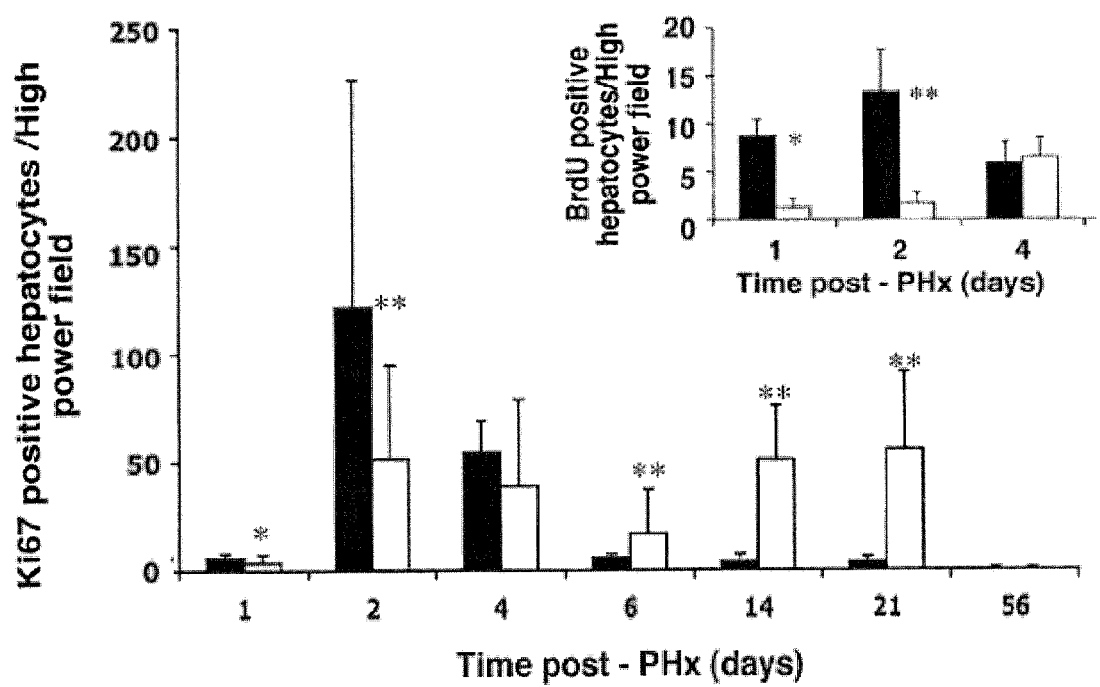
Figure 2C:
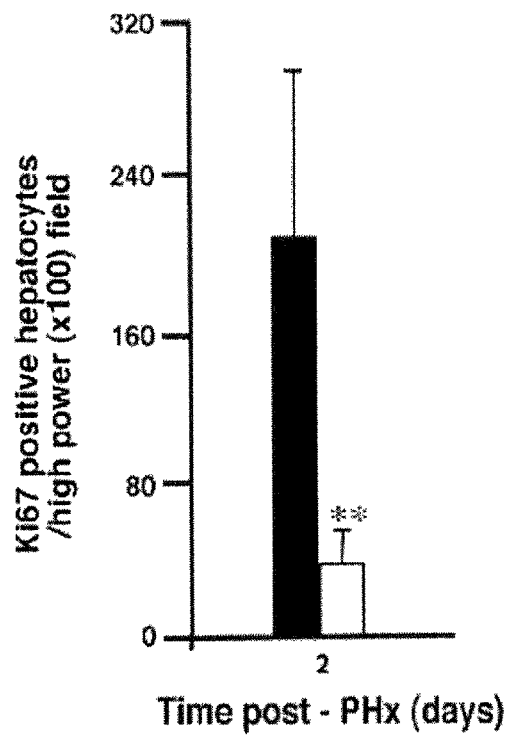
Figure 2D:
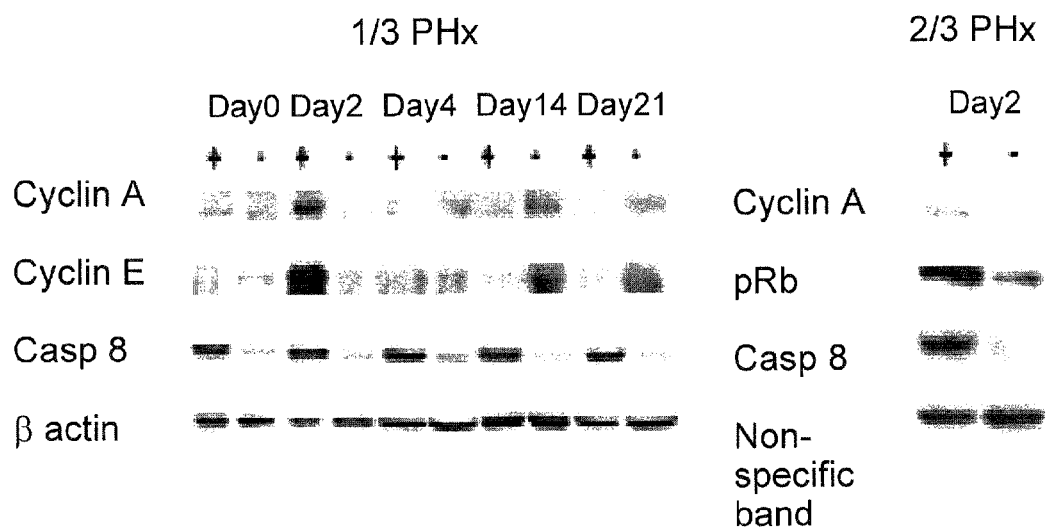
Figure 2E:
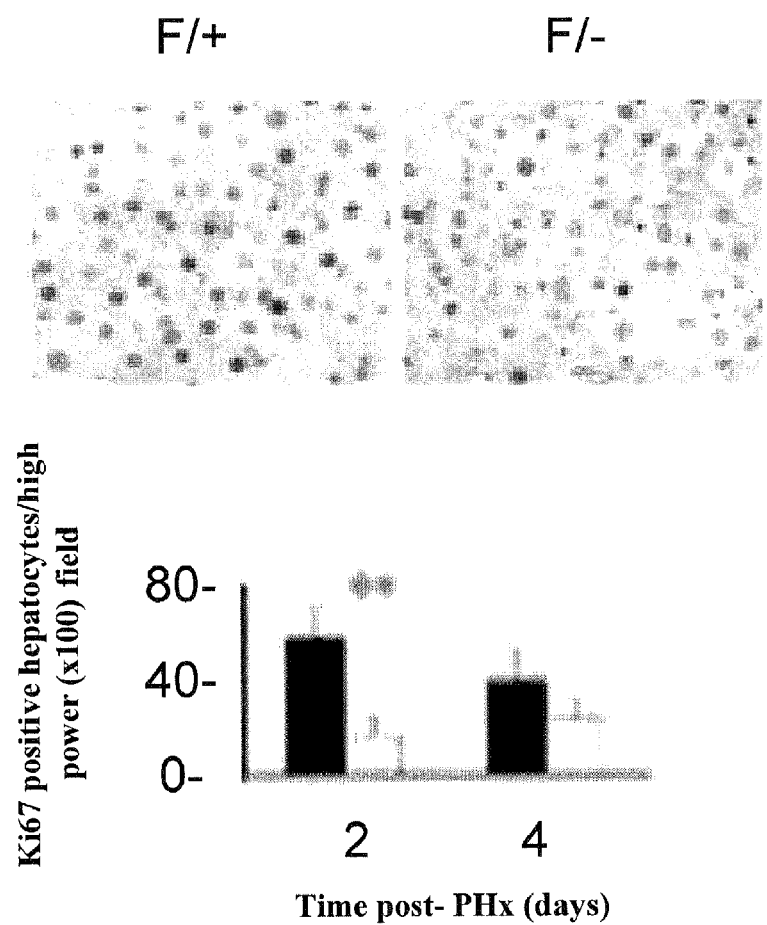

On assessing hepatocyte proliferation at a later stage after hepatectomy, it was found that whereas in the control mice cell proliferation in the liver had subsided after the initial burst, proliferation of the hepatocytes of the Casp8$^{F/-}$:Alb-Cre mice persisted for several weeks after dissection; thus eventually, despite its initial suppression, it significantly exceeded that of the normal mice (FIG. 2A lower panels, and 2B). A similar late persistent post-PHx increase was observed in hepatocyte levels of cyclin A and E (FIG. 2D).

Example 5

Effects of Caspase-8 Deficiency in Hepatocytes on Recovery from Phx: A Chronic Inflammatory Response The present observation that Casp8$^{F/-}$:Alb-Cre hepatocytes continued to proliferate long after PHx would appear to be consistent with the continuously increasing size of the liver in these mice at a late stage after hepatectomy. However, the fact that this more rapid volume increase was already discernible a few days after hepatectomy (FIG. 3D), when the proliferation rate of the caspase-8-deficient hepatocytes was still lower than normal, suggested that additional factors contribute to this difference as well.

A functional MRI protocol combined with hypercapnia and hyperoxia provides a sensitive measure of perfusion and hemodynamic alterations resulting from a variety of pathological changes (Barash et al., 2006). In this study, in control mice PHx was followed by a decrease in both $\Delta$Sco$_2$ and $\Delta$So$_2$, reflecting a decrease in liver vascularity and blood content. In contrast, in the livers of Casp8$^{F/-}$:Alb-Cre mice, 4 days after PHx both parameters were increased (FIG. 4), as a result of increased blood volume and flow. Such an increase was found to occur in association with an inflammatory state (Barash H, unpublished data). Histological analysis indeed revealed a massive accumulation of leukocytes in the livers of the nepatectomized Casp8$^{F/-}$:Alb-Cre mice, indicative of inflammation. Staining with the anti-F4/80 antibody indicated that the accumulating leukocytes are macrophages (FIG. 5A, B). Western analysis revealed a significant increase of phosphorylated STAT-3, a signaling protein activated during inflammation, in the livers of the Casp8$^{F/-}$:Alb-Cre mice (FIG. 5C).

As mentioned above, inflammation and enhanced hepatocyte proliferation in the Casp8$^{F/-}$:Alb-Cre mice were also observed after their infection with *L. monocytogenes* (FIG. 1D, E, H, I). Our mice were kept in a specific pathogen-free facility; nevertheless, in view of this effect of *Listeria* infection it was attempted to further exclude the possibility that the inflammation and enhanced liver growth observed after PHx reflect an effect of some pathogen that had escaped our notice. Accordingly, the experiments were repeated with mice that were rederived by cesarean section, placed with foster gnotobiotic mothers, and then maintained in germ-free isolators. It was found that partial hepatectomy of these rederived mice initiated the same chronic inflammatory state as that observed before rederiving (data not shown).

Example 6

Effects of Caspase-8 Deficiency in Hepatocytes on Recovery from Partial Hepatectomy: Persistent Late Hepatocyte Proliferation Occurs as a Consequence of the Chronic Inflammatory Response Comparative histological analyses of different sections from the livers of hepatectomized Casp8$^{F/-}$:Alb-Cre mice during the time of persistent hepatocyte proliferation disclosed that variation between sections in the extent of cell growth correlated with the numbers of macrophages that accumulated in the corresponding regions (FIG. 5B), suggesting that hepatocyte proliferation and the inflammatory state of the liver are causally related. To further examine this relationship mice were injected with gadolinium chloride, an agent that induces transient depletion of Kupffer cells (Canbay et al., 2003), on days 10 and 12 after PHx, the time at which the inflammation reached its climax. As shown in FIG. 5B (bottom panel) and FIG. 6, in addition to substantially decreasing the inflammatory cells that had accumulated in the Casp8$^{F/-}$:Alb-Cre liver, this treatment also practically wiped out the increase in hepatocyte proliferation in these mice. Moreover, the excessive increase in the size of their livers (probably due in part to an inflammation-related increase in blood volume and flow and in Kupffer cell numbers, and in part to an increase in hepatocyte number that mainly occurs at that time) was curtailed. These findings indicate that the constitutive growth of hepatocytes in Casp8$^{F/-}$:Alb-Cre mice at a late stage after hepatectomy is a consequence of the persistent inflammation that occurs in their livers.

References

Abramovitch R, Frenkiel D, Neeman M. Analysis of subcutaneous angiogenesis by gradient echo magnetic resonance imaging. Magn Reson Med; 39:813-824 (1998).

Abramovitch R, Dafni H, Smouha E, Benjamin L E, Neeman M. In vivo prediction of vascular susceptibility to vascular susceptibility endothelial growth factor withdrawal: magnetic resonance imaging of C6 rat glioma in nude mice. Cancer Res 59:5012-5016 (1999).

Adachi M, Suematsu S, Kondo T, Ogasawara J, Tanaka T, Yoshida N, Nagata S. Targeted mutation in the Fas gene causes hyperplasia in peripheral lymphoid organs and liver. Nat Genet. 11:294-300 (1995).

Alam A, Cohen L Y, Aouad S, Sekaly R P. Early activation of caspases during T lymphocyte stimulation results in selective substrate cleavage in nonapoptotic cells. J Exp Med 190: 1879-1890 (1999).

Anders R A, Subudhi S K, Wang J, Pfeffer K, Fu Y X. Contribution of the lymphotoxin beta receptor to liver regeneration. J Immunol 175:1295-1300 (2005).

Barash H, Gross E, Matot I, Edrei Y, Tsarfaty G, Spira G, Vlodavsky I, et al. Functional MRI during hypercapnia and hyperoxia: a non-invasive monitoring toll for changes in liver perfusion and hemodynamics in a rat model. Radiology (in press) 2006.

Beisner D R, Ch'en I L, Kolla R V, Hoffmann A, Hedrick S M. Cutting edge: innate immunity conferred by B cells is regulated by caspase-8. J Immunol 175:3469-3473 (2005).

Boldin M P, Goncharov T M, Goltsev Y V, Wallach D. Involvement of MACH, a novel MORT1/FADD-interacting protease, in Fas/APO-1- and TNF receptor-induced cell death. Cell 85:803-815 (1996).

Canbay A, Feldstein A E, Higuchi H, Werneburg N, Grambihler A, Bronk S F, Gores G J. Kupffer cell engulfment of apoptotic bodies stimulates death ligand and cytokine expression. HEPATOLOGY 38:1188-1198 (2003).

Chun H J, Zheng L, Ahmad M, Wang J, Speirs C K, Siegel R M, Dale J K, et al. Pleiotropic defects in lymphocyte activation caused by caspase-8 mutations lead to human immunodeficiency. Nature 419:395-399 (2002).

Diehl A M. Cytokine regulation of liver injury and repair. Immunol Rev 174:160-171 (2000).

Fausto N, Campbell J S, Richle K J. Liver regeneration. HEPATOLOGY 43:S45-53 (2006).

Fiume L, Di Stefano G, Busi C, Mattioli A, Bonino F, Torrani-Cerenzia M, Verme G, Rapicetta M, Bertini M, Gervasi G B. Liver targeting of antiviral nucleoside analogues through the asialoglycoprotein receptor. J Viral Hepat. 1997; 4(6):363-70. Review.

Greene A K, Puder M. Partial hepatectomy in the mouse: technique and perioperative management. J Invest Surg 16:99-102 (2003).

Groman E V, Enriquez P M, Jung C, Josephson L. Related Arabinogalactan for hepatic drug deiivery. Bioconjug Chem. 5(6):547-56 (1994).

Gruenheid S, Gros P. Related Genetic susceptibility to intracellular infections: Nramp1, macrophage function and divalent cations transport. Curr Opin Microbiol February; 3(1):43-8 (2000).

Higgins G M A R. Restoration of the liver of the white rat following partial surgical removal. Arch Pathol 1931; 12:186-202.

Hunter T, Hunt T, Jackson R J, Robertson H D. The characteristics of inhibition of protein synthesis by double-stranded ribonucleic acid in reticulocyte lysates. J Biol Chem 250(2):409-17 (1975).

Kang T B, Ben-Moshe T, Varfolomeev E E, Pewzner-Jung Y, Yogev N, Jurewicz A, Waisman A, et al. Caspase-8 serves both apoptotic and nonapoptotic roles. J Immunol 173:2976-2984 (2004).

Kellendonk C, Opherk C, Anlag K, Schutz G, Tronche F. Hepatocyte-specific expression of Cre recombinase. Genesis 26:151-153 (2000).

Kennedy N J, Kataoka T, Tschopp J, Budd R C. Caspase activation is required for T cell proliferation. J Exp Med 190:1891-1896 (1999).

Lee D S, Gil W T, Lee H H, et al. Factors affecting graft survival after living donor liver transplantation. Transplant Proc. 36:2255-2256 (2004)

Martinon F, Tschopp J. Inflammatory caspases: linking an intracellular innate immune system to autoinflammatory diseases. Cell 117:561-574 (2004).

Michalopoulos G K, DeFrances M C. Liver regeneration. Science 276:60-66 (1997).

Muzio M, Chinnaiyan A M, Kischkel F C, O'Rourke K, Shevchenko A, Ni J, Scaffidi C, et al. FLICE, a novel FADD-homologous ICE/CED-3-like protease, is recruited to the CD95 (Fas/APO-1) death—inducing signaling complex. Cell 85:817-827 (1996).

Newton K, Harris A W, Bath M L, Smith K G, Strasser A. A dominant interfering mutant of FADD/MORT1 enhances deletion of autoreactive thymocytes and inhibits proliferation of mature T lymphocytes. EMBO J. 17:706-718 (1998).

Sakamaki K, Inoue T, Asano M, Sudo K, Kazama H, Sakagami J, Sakata S, et al. Ex vivo whole-embryo culture of caspase-8-deficient embryos normalize their aberrant phenotypes in the developing neural tube and heart. Cell Death Differ 9:1196-1206 (2002).

Saleh M, Mathison J C, Wolinski M K, Bensinger S J, Fitzgerald P, Droin N, Ulevitch R J, et al. Enhanced bacterial clearance and sepsis resistance in caspase-12-deficient mice. Nature 440:1064-1068 (2006).

Salmena L, Lemmers B, Hakem A, Matysiak-Zablocki E, Murakami K, Au P Y, Berry D M, et al. Essential role for caspase 8 in T-cell homeostasis and T-cell-mediated immunity. Genes Dev 17:883-895 (2003).

Shi Y. Mechanisms of caspase activation and inhibition during apoptosis. Mol Cell 9:459-470 (2002).

Steinert M, Hentschel U, Hacker J. *Legionella pneumophila*: an aquatic microbe goes astray. FEMS Microbiol Rev. (2):149-62 (2002)

Su H, Bidere N, Zheng L, Cubre A, Sakai K, Dale J, Salmena L, et al. Requirement for caspase-8 in NF-kappaB activation by antigen receptor. Science 307:1465-1468 (2005).

Varfolomeev E E, Schuchmann M, Luria V, Chiannilkulchai N, Beckmann J S, Mett I L, Rebrikov D, et al. Targeted disruption of the mouse Caspase 8 gene ablates cell death induction by the TNF receptors, Fas/Apol, and DR3 and is lethal prenatally. Immunity 9:267-276 (1998).

Wallach D, Varfolomeev E E, Malinin N L, Goltsev Y V, Kovalenko A V, Boldin M P. Tumor necrosis factor receptor and Fas signaling mecnanisms. Annu Rev Immunol 17:331-367 (1999).

Walsh C M, Wen B G, Chinnaiyan A M, O'Rourke K, Dixit V M, Hedrick S M. A role for FADD in T cell activation and development. Immunity 8:439-449 (1998).

Wing E J, Gregory S H. *Listeria monocytogenes*: clinical and experimental update. J Infect Dis 185 Suppl 1:S18-24 (2002).

Wu J, Nantz M H, Zern M A. Targeting hepatocytes for drug and gene delivery: emerging novel approaches and applications. Front Biosci. 7:d717-25. Review (2002).

Wu Y T, Jiaang W T, Lin K G, Huang C M, Chang C H, Sun Y L, Fan K H, Hsu W C, Wang H E, Lin S B, Chen S T. A new N-acetylgalactosamine containing peptide as a targeting vehicle for mammalian hepatocytes via asialoglycoprotein receptor endocytosis. Curr Drug Deliv. (2):119-27 (2004).

Zhang J, Cado D, Chen A, Kabra N H, Winoto A. Fas-mediated apoptosis and activation-induced T-cell proliferation are defective in mice lacking FADD/Mortl. Nature 392:296-300 (1998).

Zimmers T A, McKillop I H, Pierce R H, Yoo J Y, Koniaris L G. Massive liver growth in mice induced by systemic interleukin 6 administration. HEPATOLOGY 38:326-334 (2003).

The invention claimed is:

1. A method for treating a *Listeria* bacterial infection in a patient comprising administering to said patient a therapeutically effective amount of at least one agent selected from the group consisting of caspase-8, a mutein comprising an amino acid sequence at least 90% identical to that of caspase-8 or a functional derivative or salt of caspase-8 or said mutein, wherein said functional derivative is derived by one or more derivatizations selected independently from the group consisting of attachment of polyethylene glycol to an amino acid side chain, esterification with an aliphatic ester of a carboxyl group, amidation of a carboxyl group, N-acyl derivatization of an amino group, and O-acyl derivatization of a hydroxyl group; whereby said *Listeria* bacterial infection is treated.

2. The method according to claim 1, wherein infection develops in an organ or tissue comprising cells in which caspase-8 level and/or activity is down regulated.

3. The method according to claim 2, wherein the organ or tissue is the liver.

4. The method according to claim 2, wherein the cells are hepatocytes.

5. The method according to claim 1, wherein the *Listeria* is *Listeria monocytogenes*.

* * * * *

```
                          SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: synthetic

<400> SEQUENCE: 1

Trp Glu His Asp
1

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Val Asp Val Ala Asp
1               5

<210> SEQ ID NO 3
<211> LENGTH: 4
<212> TYPE: PRT
<213> ORGANISM: Artificial Sequence
<220> FEATURE:
<223> OTHER INFORMATION: synthetic

<400> SEQUENCE: 3

Asp Glu Val Asp
1

<210> SEQ ID NO 4
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Ile is derivatized by a benzyloxycarboxyl
      group.
<220> FEATURE:
<221> NAME/KEY: misc_feature
<222> LOCATION: (4)..(4)
<223> OTHER INFORMATION: Asp is derivatized by fluoromethyl ketone.

<400> SEQUENCE: 4

Ile Glu Thr Asp
1

<210> SEQ ID NO 5
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Asp is derivatized by fluoromethyl ketone.

<400> SEQUENCE: 5

Ile Glu Thr Asp
1
```